US009044020B2

(12) United States Patent
Chang et al.

(10) Patent No.: US 9,044,020 B2
(45) Date of Patent: Jun. 2, 2015

(54) ISOLATED NUCLEOTIDE MOLECULE AND METHOD OF SENSING AND KILLING OF PATHOGENIC MICROORGANISM

(75) Inventors: Matthew Wook Chang, Singapore (SG); Chueh Loo Poh, Singapore (SG); Choon Kit Wong, Singapore (SG); Nazanin Saeidi, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 13/586,657

(22) Filed: Aug. 15, 2012

(65) Prior Publication Data

US 2013/0052164 A1     Feb. 28, 2013

Related U.S. Application Data

(60) Provisional application No. 61/529,417, filed on Aug. 31, 2011.

(51) Int. Cl.

| | |
|---|---|
| *A01N 63/02* | (2006.01) |
| *A61P 31/04* | (2006.01) |
| *A01P 1/00* | (2006.01) |
| *C12N 1/21* | (2006.01) |
| *A61K 35/74* | (2006.01) |
| *C12N 15/70* | (2006.01) |
| *A61K 38/16* | (2006.01) |
| *A01N 37/46* | (2006.01) |

(52) U.S. Cl.
CPC ............... *A01N 63/02* (2013.01); *C12N 15/70* (2013.01); *A61K 38/164* (2013.01); *A01N 37/46* (2013.01)

(58) Field of Classification Search
None
See application file for complete search history.

(56) References Cited

PUBLICATIONS

Choudhary et al. Appl Microbiol Biotechnol, Mar. 2010, 86:1267-1279.*
Anderson et al., "Environmentally Controlled Invasion of Cancer Cells by Engineered Bacteria,"*J Mol Biol* 355:619-627, 2006.
Asad et al., "Bench-to-bedside review: Quorum sensing and the role of cell-to-cell communication during invasive bacterial infection," *Crit Care* 12:236, 2008, 11 pages.
Baba et al., "Instruments of microbial warfare: bacteriocin synthesis, toxicity and immunity," *Trends Microbiol* 6(2):66-71, Feb. 1998.
Bradford, "A Rapid and Sensitive Method for the Quantitation of Microgram Quantities of Protein Utilizing the Principle of Protein-Dye Binding." *Anal Biochem* 72:248-254, 1976.
Canton et al., "Refinement and standardization of synthetic biological parts and devices," *Nat Biotechnol* 26(7):787-793, 2008.
Chak et al., "Cloning and characterization of the ColE7 plasmid," *J Gen Microbiol* 137:91-100, 1991.

Chang et al., "Microarray analysis of *Pseudomonas aeruginosa* reveals induction of pyocin genes in response to hydrogen peroxide," *BMC Genomics* 6:115, 2005, 14 pages.
Chang et al., "Microarray Analysis of Toxicogenomic Effects of Peracetic Acid on *Pseudomonas aeruginosa*," *Environ Sci Technol* 39(15):5893-5899, 2005.
Charlson et al., "Disordered Microbial Communities in the Upper Respiratory Tract of Cigarette Smokers," *PLoS ONE* 5(12):e15216, Dec. 2010, 10 pages.
Charlton et al., "A novel and sensitive method for the quantification of N-3-oxoacyl homoserine lactones using gas chromatography-mass spectrometry: application to a model bacterial biofilm," *Environ Microbiol* 2(5):530-541, 2000.
Chen et al., "Adsorptive refolding of a highly disulfide-bonded inclusion body protein using anion-exchange chromatography," *J Chromatogr A* 1216:4877-4886, 2009.
Choi et al., "A 10-min method for preparation of highly electrocompetent *Pseudomonas aeruginosa* cells: application for DNA fragment transfer between chromosomes and plasmid transformation," *J Microbial Methods* 64:391-397, 2006.
Endy, "Foundations for engineering biology," *Nature* 438:449-453, Nov. 24, 2005.
Gray et al., "Interchangeability and Specificity of Components from the Quorum-Sensing Regulatory Systems of *Vibrio fischeri* and *Pseudomonas aeruginosa*," *J Bacterial* 176(10):3076-3080, May 1994.
Huang et al., "Soluble fusion expression and characterization of bioactive human beta-defensin 26 and 27,"*Appl Microbial Biotechnol* 84: 301-308, 2009.
Lin et al., "Induction of membrane permeability in *Escherichia coli* mediated by lysis protein of the ColE7 operon," *FEMS Microbial Lett* 298:85-92, 2009.
Ling et al., "A predicted S-type pyocin shows a bactericidal activity against clinical *Pseudomonas aeruginosa* isolates through membrane damage," *FEBS Lett* 584:3354-3358, 2010.
Pearson et al., "A second N-acylhomoserine lactone signal produced by *Pseudomonas aeruginosa*," *Proc Natl Acad Sci USA* 92:1490-1494, Feb. 1995.
Ro et al., "Production of the antimalarial drug precursor artemisinic acid in engineered yeast," *Nature* 440:940-943, Apr. 13, 2006.
Scholl et al., "Antibacterial Efficacy of R-Type Pyocins towards *Pseudomonas aeruginosa* in a Murine Peritonitis Model," *Antimicrob Agents Chemother* 52(5):1647-1652, May 2008.
Schuster et al., "Promoter specificity in *Pseudomonas aeruginosa* quorum sensing revealed by DNA binding of purified LasR," *Proc Natl Acad Sci USA* 101(45): 15833-15839, Nov. 9, 2004.

(Continued)

*Primary Examiner* — Doug Schultz
(74) *Attorney, Agent, or Firm* — Seed IP Law Group, PLLC

(57) ABSTRACT

The present invention relates to an isolated nucleic acid molecule comprising a first nucleotide sequence encoding a protein that detects the presence, amount or both of a pathogenic microorganism by forming a complex with a protein produced by said pathogenic microorganism; a second nucleotide sequence encoding an antimicrobial peptide, wherein the antimicrobial peptide is effective against the pathogenic microorganism detected by the protein encoded by the first nucleotide sequence, wherein the second nucleotide sequence is under control of a promoter that is induced by the complex of the protein encoded by the first nucleotide sequence and the protein produced by said pathogenic microorganism. A recombinant microorganism comprising the isolated nucleic acid molecule and a method of sensing and killing pathogenic microorganisms is also described.

25 Claims, 23 Drawing Sheets

(56) References Cited

PUBLICATIONS

Seo et al., "Purification of the pyocin S2 complex from *Pseudomonas aeruginosa* PAO1: analysis of DNase activity," *Biochem Biophys Res Commun* 172(2):455-461, 1990.

Sinha et al., "Reprogramming bacteria to seek and destroy an herbicide," *Nat Chem Biol* 6:464-470, Jun. 2010.

Small et al., "Comparative global transcription analysis of sodium hypochlorite, peracetic acid, and hydrogen peroxide on *Pseudomonas aeruginosa*," *Appl Microbial Biotechnol* 76:1093-1105, 2007.

Smith et al., "The pyocin Sa Receptor of *Pseudomonas aeruginosa* Is Associated with Ferripyoverdin Uptake," *J Bacteriol* 174(14):4847-4849, Jul. 1992.

Smith et al., "Signal Discrimination by Differential Regulation of Protein Stability in Quorum Sensing," *J Mol Biol* 382:1290-1297, 2008.

Steen et al., "Microbial production of fatty-acid-derived fuels and chemicals from plant biomass," *Nature* 463:559-563, Jan. 2010.

Wright et al., "A controlled clinical trial of a therapeutic bacteriophage preparation in chronic otitis due to antibiotic-resistant *Pseudomonas aeruginosa*; a preliminary report of efficacy," *Clin Otolaryngol* 34:349-357, 2009.

* cited by examiner

Exposed to supernatant of engineered E. coli induced with native 3OC$_{12}$HSL

Exposed to supernatant of wild-type E. coli

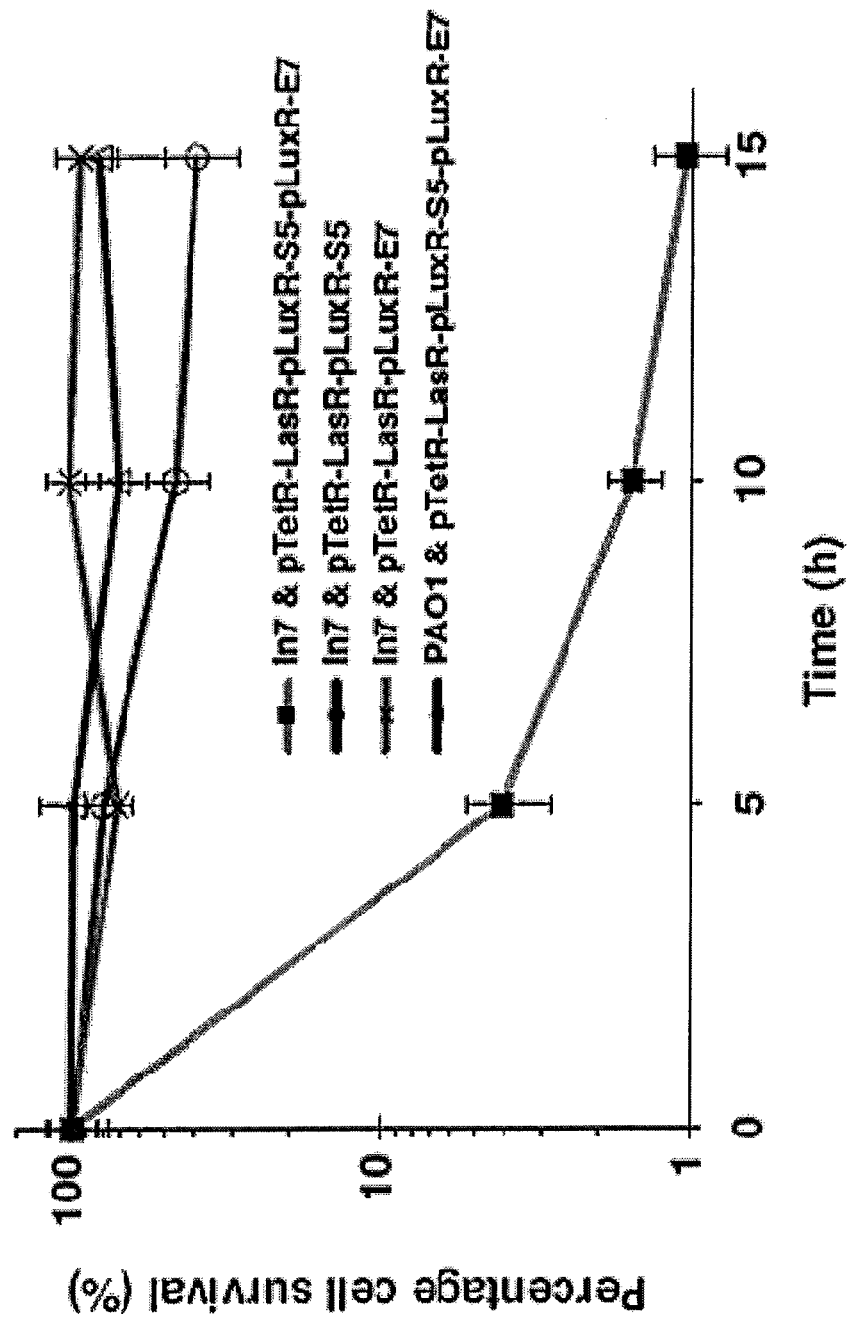

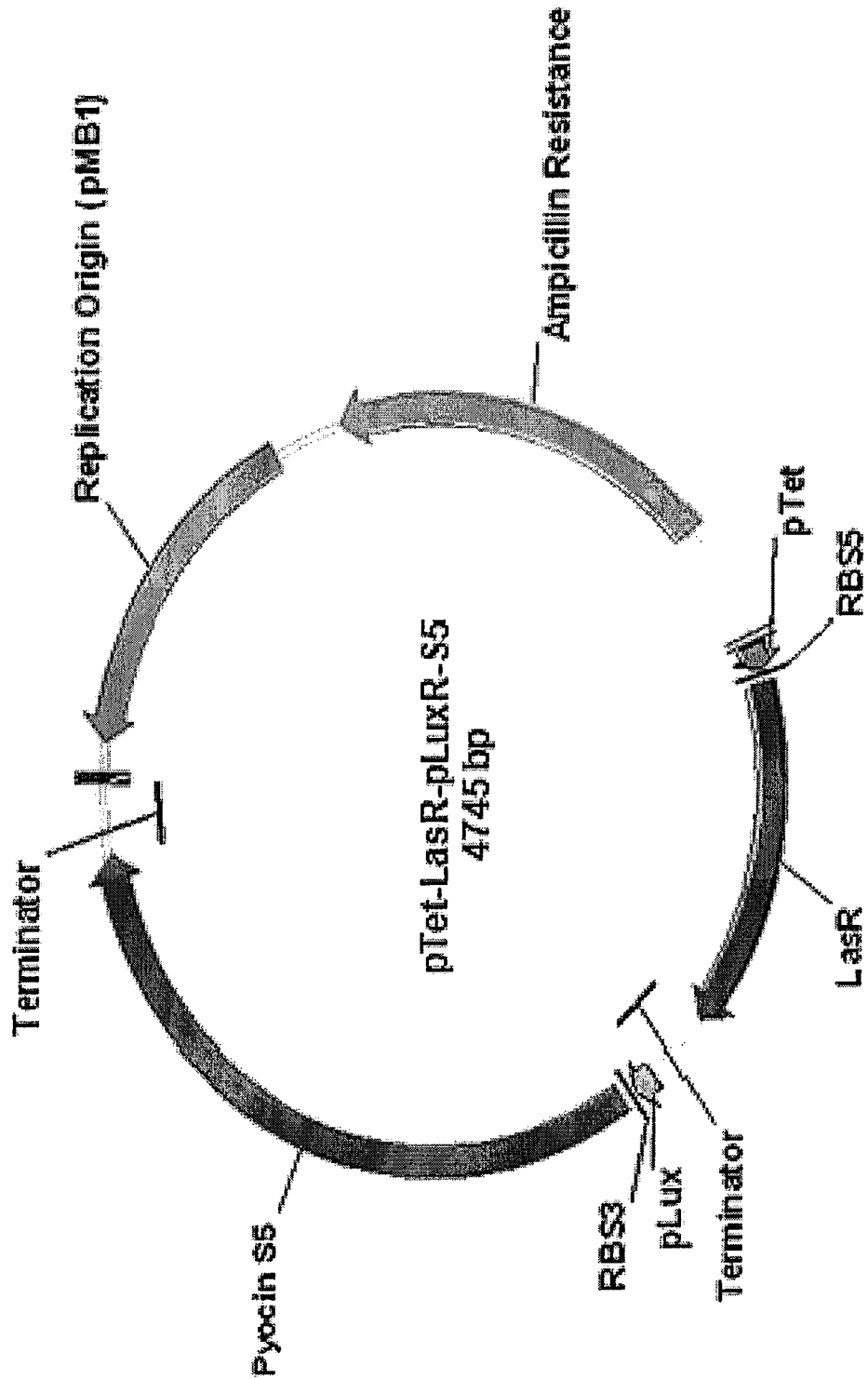

| Part Abbreviation | Description | Symbol |
|---|---|---|
| pTetR | tetR constitutive promoter |  pTetR |
| pLuxR | luxR quorum sensing promoter |  pLuxR |
| rbs3 | Ribosome binding site (medium) |  rbs3 |
| rbs5 | Ribosome binding site (strong) |  rbs5 |
| T15 | Double terminator |  T15 |
| LasR | LasR coding gene |  LasR |
| GFP | GFP coding gene |  GFP |
| E7 | E7 lysis coding gene |  E7 |
| S5 | Pyocin S5 coding gene |  S5 |

| Part Abbreviation | Description | Symbol |
|---|---|---|
| pTetR-LasR-pLuxR | Sensing device | pTetR rbs5 LasR T15 pLuxR |
| pTetR-LasR-pLuxR-GFP | Sensing device with GFP reporter | pTetR rbs5 LasR T15 pLuxR rbs3 GFP T15 |
| pTetR-LasR-pLuxR-S5 | Sensing device with pyocin S5 gene | pTetR rbs5 LasR T15 pLuxR rbs5 S5 T15 |
| pTetR-LasR-pLuxR-E7 | Sensing device with E7 lysis gene | pTetR rbs5 LasR T15 pLuxR rbs3 E7 T15 |
| pTetR-LasR-pLuxR-S5-pLux-E7 | Sensing/Killing system construct | pTetR rbs5 LasR T15 pLuxR rbs5 S5 T15<br>pLuxR rbs3 E7 T15 |

FIG. 9B

SEQUENCE LISTING

```
<160> NUMBER OF SEQ ID NOS: 6

<210> SEQ ID NO 1
<211> LENGTH: 239
<212> TYPE: PRT
<213> ORGANISM: Pseudomonas aeruginosa

<400> SEQUENCE: 1

Met Ala Leu Val Asp Gly Phe Leu Glu Leu Glu Arg Ser Ser Gly Lys
1               5                   10                  15

Leu Glu Trp Ser Ala Ile Leu Gln Lys Met Ala Ser Asp Leu Gly Phe
            20                  25                  30

Ser Lys Ile Leu Phe Gly Leu Leu Pro Lys Asp Ser Gln Asp Tyr Glu
        35                  40                  45

Asn Ala Phe Ile Val Gly Asn Tyr Pro Ala Ala Trp Arg Glu His Tyr
    50                  55                  60
```

```
Asp Arg Ala Gly Tyr Ala Arg Val Asp Pro Thr Val Ser His Cys Thr
 65                  70                  75                  80

Gln Ser Val Leu Pro Ile Phe Trp Glu Pro Ser Ile Tyr Gln Thr Arg
                 85                  90                  95

Lys Gln His Glu Phe Phe Glu Glu Ala Ser Ala Ala Gly Leu Val Tyr
            100                 105                 110

Gly Leu Thr Met Pro Leu His Gly Ala Arg Gly Glu Leu Gly Ala Leu
            115                 120                 125

Ser Leu Ser Val Glu Ala Glu Asn Arg Ala Glu Ala Asn Arg Phe Ile
130                 135                 140

Glu Ser Val Leu Pro Thr Leu Trp Met Leu Lys Asp Tyr Ala Leu Gln
145                 150                 155                 160

Ser Gly Ala Gly Leu Ala Phe Glu His Pro Val Ser Lys Pro Val Val
                165                 170                 175

Leu Thr Ser Arg Glu Lys Glu Val Leu Gln Trp Cys Ala Ile Gly Lys
            180                 185                 190

Thr Ser Trp Glu Ile Ser Val Ile Cys Asn Cys Ser Glu Ala Asn Val
            195                 200                 205

Asn Phe His Met Gly Asn Ile Arg Arg Lys Phe Gly Val Thr Ser Arg
        210                 215                 220

Arg Val Ala Ala Ile Met Ala Val Asn Leu Gly Leu Ile Thr Leu
225                 230                 235

<210> SEQ ID NO 2
<211> LENGTH: 515
<212> TYPE: PRT
<213> ORGANISM: Unknown
<220> FEATURE:
<223> OTHER INFORMATION: Regulatory protein LuxR (Aliivibrio fischeri
      (Vibrio fischeri))-Pyocin S5

<400> SEQUENCE: 2

Thr Cys Arg Ile Val Gln Val Tyr Ala Arg Lys Trp Phe Val Ile Val
 1               5                  10                  15

Glu Met Ser Asn Asp Asn Glu Val Pro Gly Ser Met Val Ile Val Ala
                 20                  25                  30

Gln Gly Pro Asp Asp Gln Tyr Ala Tyr Glu Val Pro Pro Ile Asp Ser
             35                  40                  45

Ala Ala Val Ala Gly Asn Met Phe Gly Asp Leu Ile Gln Arg Glu Ile
         50                  55                  60

Tyr Leu Gln Lys Asn Ile Tyr Tyr Pro Val Arg Ser Ile Phe Glu Gln
 65                  70                  75                  80

Gly Thr Lys Glu Lys Lys Glu Ile Asn Lys Lys Val Ser Asp Gln Val
                 85                  90                  95

Asp Gly Leu Leu Lys Gln Ile Thr Gln Gly Lys Arg Glu Ala Thr Arg
            100                 105                 110

Gln Glu Arg Val Asp Val Met Ser Ala Val Leu His Lys Met Glu Ser
            115                 120                 125

Asp Leu Glu Gly Tyr Lys Lys Thr Phe Thr Lys Gly Pro Phe Ile Asp
130                 135                 140

Tyr Glu Lys Gln Ser Ser Leu Ser Ile Tyr Glu Ala Trp Val Lys Ile
145                 150                 155                 160

Trp Glu Lys Asn Ser Trp Glu Glu Arg Lys Lys Tyr Pro Phe Gln Gln
                165                 170                 175

Leu Val Arg Asp Glu Leu Glu Arg Ala Val Ala Tyr Tyr Lys Gln Asp
```

```
            180                 185                 190
Ser Leu Ser Glu Ala Val Lys Val Leu Arg Gln Glu Leu Asn Lys Gln
        195                 200                 205

Lys Ala Leu Lys Glu Lys Glu Asp Leu Ser Gln Leu Glu Arg Asp Tyr
    210                 215                 220

Arg Thr Arg Lys Ala Asn Leu Glu Met Lys Val Gln Ser Glu Leu Asp
225                 230                 235                 240

Gln Ala Gly Ser Ala Leu Pro Pro Leu Val Ser Pro Thr Pro Glu Gln
                245                 250                 255

Trp Leu Glu Arg Ala Thr Arg Leu Val Thr Gln Ala Ile Ala Asp Lys
            260                 265                 270

Lys Gln Leu Gln Thr Thr Asn Asn Thr Leu Ile Lys Asn Ser Pro Thr
        275                 280                 285

Pro Leu Glu Lys Gln Lys Ala Ile Tyr Asn Gly Glu Leu Leu Val Asp
    290                 295                 300

Glu Ile Ala Ser Leu Gln Ala Arg Leu Val Lys Leu Asn Ala Glu Thr
305                 310                 315                 320

Thr Arg Arg Arg Thr Glu Ala Glu Arg Lys Ala Ala Glu Glu Gln Ala
                325                 330                 335

Leu Gln Asp Ala Ile Lys Phe Thr Ala Asp Phe Tyr Lys Glu Val Thr
            340                 345                 350

Glu Lys Phe Gly Ala Arg Thr Ser Glu Met Ala Arg Gln Leu Ala Glu
        355                 360                 365

Gly Ala Arg Gly Lys Asn Ile Arg Ser Ser Ala Glu Ala Ile Lys Ser
    370                 375                 380

Phe Glu Lys His Lys Asp Ala Leu Asn Lys Lys Leu Ser Leu Lys Asp
385                 390                 395                 400

Arg Gln Ala Ile Ala Lys Ala Phe Asp Ser Leu Asp Lys Gln Met Met
                405                 410                 415

Ala Lys Ser Leu Glu Lys Phe Ser Lys Gly Phe Gly Val Val Gly Lys
            420                 425                 430

Ala Ile Asp Ala Ala Ser Leu Tyr Gln Glu Phe Lys Ile Ser Thr Glu
        435                 440                 445

Thr Gly Asp Trp Lys Pro Phe Phe Val Lys Ile Glu Thr Leu Ala Ala
    450                 455                 460

Gly Ala Ala Ala Ser Trp Leu Val Gly Ile Ala Phe Ala Thr Ala Thr
465                 470                 475                 480

Ala Thr Pro Ile Gly Ile Leu Gly Phe Ala Leu Val Met Ala Val Thr
                485                 490                 495

Gly Ala Met Ile Asp Glu Asp Leu Leu Glu Lys Ala Asn Asn Leu Val
            500                 505                 510

Ile Ser Ile
        515

<210> SEQ ID NO 3
<211> LENGTH: 64
<212> TYPE: PRT
<213> ORGANISM: Unknown
<220> FEATURE:
<223> OTHER INFORMATION: Regulatory protein LuxR (Aliivibrio fischeri
      (Vibrio fischeri))-E7 protein

<400> SEQUENCE: 3

Thr Cys Arg Ile Val Gln Val Tyr Ala Arg Lys Trp Phe Val Ile Val
1               5                   10                  15
```

```
Glu Met Lys Lys Ile Thr Gly Ile Ile Leu Leu Leu Ala Ala Ile
            20                  25                  30

Ile Leu Ala Ala Cys Gln Ala Asn Tyr Ile Arg Asp Val Gln Gly Gly
        35                  40                  45

Thr Val Ser Pro Ser Ser Thr Ala Glu Leu Thr Gly Val Glu Thr Gln
    50                  55                  60

<210> SEQ ID NO 4
<211> LENGTH: 818
<212> TYPE: PRT
<213> ORGANISM: Unknown
<220> FEATURE:
<223> OTHER INFORMATION: Isolated nucleic acid molecule comprising LasR-
      pLuxR-pyocin S5-pLuxR-E7 protein

<400> SEQUENCE: 4

Met Ala Leu Val Asp Gly Phe Leu Glu Leu Glu Arg Ser Ser Gly Lys
1               5                   10                  15

Leu Glu Trp Ser Ala Ile Leu Gln Lys Met Ala Ser Asp Leu Gly Phe
            20                  25                  30

Ser Lys Ile Leu Phe Gly Leu Leu Pro Lys Asp Ser Gln Asp Tyr Glu
        35                  40                  45

Asn Ala Phe Ile Val Gly Asn Tyr Pro Ala Ala Trp Arg Glu His Tyr
    50                  55                  60

Asp Arg Ala Gly Tyr Ala Arg Val Asp Pro Thr Val Ser His Cys Thr
65                  70                  75                  80

Gln Ser Val Leu Pro Ile Phe Trp Glu Pro Ser Ile Tyr Gln Thr Arg
                85                  90                  95

Lys Gln His Glu Phe Phe Glu Glu Ala Ser Ala Ala Gly Leu Val Tyr
            100                 105                 110

Gly Leu Thr Met Pro Leu His Gly Ala Arg Gly Glu Leu Gly Ala Leu
        115                 120                 125

Ser Leu Ser Val Glu Ala Glu Asn Arg Ala Glu Ala Asn Arg Phe Ile
    130                 135                 140

Glu Ser Val Leu Pro Thr Leu Trp Met Leu Lys Asp Tyr Ala Leu Gln
145                 150                 155                 160

Ser Gly Ala Gly Leu Ala Phe Glu His Pro Val Ser Lys Pro Val Val
                165                 170                 175

Leu Thr Ser Arg Glu Lys Glu Val Leu Gln Trp Cys Ala Ile Gly Lys
            180                 185                 190

Thr Ser Trp Glu Ile Ser Val Ile Cys Asn Cys Ser Glu Ala Asn Val
        195                 200                 205

Asn Phe His Met Gly Asn Ile Arg Arg Lys Phe Gly Val Thr Ser Arg
    210                 215                 220

Arg Val Ala Ala Ile Met Ala Val Asn Leu Gly Leu Ile Thr Leu Thr
225                 230                 235                 240

Cys Arg Ile Val Gln Val Tyr Ala Arg Lys Trp Phe Val Ile Val Glu
                245                 250                 255

Met Ser Asn Asp Asn Glu Val Pro Gly Ser Met Val Ile Val Ala Gln
            260                 265                 270

Gly Pro Asp Asp Gln Tyr Ala Tyr Glu Val Pro Pro Ile Asp Ser Ala
        275                 280                 285

Ala Val Ala Gly Asn Met Phe Gly Asp Leu Ile Gln Arg Glu Ile Tyr
    290                 295                 300

Leu Gln Lys Asn Ile Tyr Tyr Pro Val Arg Ser Ile Phe Glu Gln Gly
305                 310                 315                 320
```

```
Thr Lys Glu Lys Lys Glu Ile Asn Lys Val Ser Asp Gln Val Asp
            325                 330                 335

Gly Leu Leu Lys Gln Ile Thr Gln Gly Lys Arg Glu Ala Thr Arg Gln
            340                 345                 350

Glu Arg Val Asp Val Met Ser Ala Val Leu His Lys Met Glu Ser Asp
            355                 360                 365

Leu Glu Gly Tyr Lys Lys Thr Phe Thr Lys Gly Pro Phe Ile Asp Tyr
        370                 375                 380

Glu Lys Gln Ser Ser Leu Ser Ile Tyr Glu Ala Trp Val Lys Ile Trp
385                 390                 395                 400

Glu Lys Asn Ser Trp Glu Glu Arg Lys Lys Tyr Pro Phe Gln Gln Leu
            405                 410                 415

Val Arg Asp Glu Leu Glu Arg Ala Val Ala Tyr Tyr Lys Gln Asp Ser
            420                 425                 430

Leu Ser Glu Ala Val Lys Val Leu Arg Gln Glu Leu Asn Lys Gln Lys
        435                 440                 445

Ala Leu Lys Glu Lys Glu Asp Leu Ser Gln Leu Glu Arg Asp Tyr Arg
        450                 455                 460

Thr Arg Lys Ala Asn Leu Glu Met Lys Val Gln Ser Glu Leu Asp Gln
465                 470                 475                 480

Ala Gly Ser Ala Leu Pro Pro Leu Val Ser Pro Thr Pro Glu Gln Trp
            485                 490                 495

Leu Glu Arg Ala Thr Arg Leu Val Thr Gln Ala Ile Ala Asp Lys Lys
            500                 505                 510

Gln Leu Gln Thr Thr Asn Asn Thr Leu Ile Lys Asn Ser Pro Thr Pro
        515                 520                 525

Leu Glu Lys Gln Lys Ala Ile Tyr Asn Gly Glu Leu Leu Val Asp Glu
        530                 535                 540

Ile Ala Ser Leu Gln Ala Arg Leu Val Lys Leu Asn Ala Glu Thr Thr
545                 550                 555                 560

Arg Arg Arg Thr Glu Ala Glu Arg Lys Ala Ala Glu Glu Gln Ala Leu
            565                 570                 575

Gln Asp Ala Ile Lys Phe Thr Ala Asp Phe Tyr Lys Glu Val Thr Glu
            580                 585                 590

Lys Phe Gly Ala Arg Thr Ser Glu Met Ala Arg Gln Leu Ala Glu Gly
        595                 600                 605

Ala Arg Gly Lys Asn Ile Arg Ser Ser Ala Glu Ala Ile Lys Ser Phe
        610                 615                 620

Glu Lys His Lys Asp Ala Leu Asn Lys Lys Leu Ser Leu Lys Asp Arg
625                 630                 635                 640

Gln Ala Ile Ala Lys Ala Phe Asp Ser Leu Asp Lys Gln Met Met Ala
            645                 650                 655

Lys Ser Leu Glu Lys Phe Ser Lys Gly Phe Gly Val Val Gly Lys Ala
            660                 665                 670

Ile Asp Ala Ala Ser Leu Tyr Gln Glu Phe Lys Ile Ser Thr Glu Thr
        675                 680                 685

Gly Asp Trp Lys Pro Phe Phe Val Lys Ile Glu Thr Leu Ala Ala Gly
        690                 695                 700

Ala Ala Ala Ser Trp Leu Val Gly Ile Ala Phe Ala Thr Ala Thr Ala
705                 710                 715                 720

Thr Pro Ile Gly Ile Leu Gly Phe Ala Leu Val Met Ala Val Thr Gly
            725                 730                 735
```

```
Ala Met Ile Asp Glu Asp Leu Leu Glu Lys Ala Asn Asn Leu Val Ile
            740                 745                 750

Ser Ile Thr Cys Arg Ile Val Gln Val Tyr Ala Arg Lys Trp Phe Val
            755                 760                 765

Ile Val Glu Met Lys Lys Ile Thr Gly Ile Ile Leu Leu Leu Leu Ala
            770                 775                 780

Ala Ile Ile Leu Ala Ala Cys Gln Ala Asn Tyr Ile Arg Asp Val Gln
785                 790                 795                 800

Gly Gly Thr Val Ser Pro Ser Ser Thr Ala Glu Leu Thr Gly Val Glu
            805                 810                 815

Thr Gln

<210> SEQ ID NO 5
<211> LENGTH: 257
<212> TYPE: PRT
<213> ORGANISM: Unknown
<220> FEATURE:
<223> OTHER INFORMATION: TetR promoter-transcriptional regulator LasR

<400> SEQUENCE: 5

Ser Leu Ser Val Ile Glu Ile Asp Ile Pro Ile Ser Asp Arg Asp Thr
1               5                   10                  15

Glu His Met Ala Leu Val Asp Gly Phe Leu Glu Leu Glu Arg Ser Ser
            20                  25                  30

Gly Lys Leu Glu Trp Ser Ala Ile Leu Gln Lys Met Ala Ser Asp Leu
        35                  40                  45

Gly Phe Ser Lys Ile Leu Phe Gly Leu Leu Pro Lys Asp Ser Gln Asp
    50                  55                  60

Tyr Glu Asn Ala Phe Ile Val Gly Asn Tyr Pro Ala Ala Trp Arg Glu
65                  70                  75                  80

His Tyr Asp Arg Ala Gly Tyr Ala Arg Val Asp Pro Thr Val Ser His
                85                  90                  95

Cys Thr Gln Ser Val Leu Pro Ile Phe Trp Glu Pro Ser Ile Tyr Gln
            100                 105                 110

Thr Arg Lys Gln His Glu Phe Phe Glu Glu Ala Ser Ala Ala Gly Leu
        115                 120                 125

Val Tyr Gly Leu Thr Met Pro Leu His Gly Ala Arg Gly Glu Leu Gly
    130                 135                 140

Ala Leu Ser Leu Ser Val Glu Ala Glu Asn Arg Ala Glu Ala Asn Arg
145                 150                 155                 160

Phe Ile Glu Ser Val Leu Pro Thr Leu Trp Met Leu Lys Asp Tyr Ala
                165                 170                 175

Leu Gln Ser Gly Ala Gly Leu Ala Phe Glu His Pro Val Ser Lys Pro
            180                 185                 190

Val Val Leu Thr Ser Arg Glu Lys Glu Val Leu Gln Trp Cys Ala Ile
        195                 200                 205

Gly Lys Thr Ser Trp Glu Ile Ser Val Ile Cys Asn Cys Ser Glu Ala
    210                 215                 220

Asn Val Asn Phe His Met Gly Asn Ile Arg Arg Lys Phe Gly Val Thr
225                 230                 235                 240

Ser Arg Arg Val Ala Ala Ile Met Ala Val Asn Leu Gly Leu Ile Thr
                245                 250                 255

Leu

<210> SEQ ID NO 6
```

<211> LENGTH: 836
<212> TYPE: PRT
<213> ORGANISM: Unknown
<220> FEATURE:
<223> OTHER INFORMATION: Isolated nucleic acid molecule comprising ptetR-LasR-pLuxR-pyocin S5-pLuxR-E7 protein

<400> SEQUENCE: 6

```
Ser Leu Ser Val Ile Glu Ile Asp Ile Pro Ile Ser Asp Arg Asp Thr
1               5                   10                  15
Glu His Met Ala Leu Val Asp Gly Phe Leu Glu Leu Glu Arg Ser Ser
            20                  25                  30
Gly Lys Leu Glu Trp Ser Ala Ile Leu Gln Lys Met Ala Ser Asp Leu
        35                  40                  45
Gly Phe Ser Lys Ile Leu Phe Gly Leu Leu Pro Lys Asp Ser Gln Asp
    50                  55                  60
Tyr Glu Asn Ala Phe Ile Val Gly Asn Tyr Pro Ala Ala Trp Arg Glu
65                  70                  75                  80
His Tyr Asp Arg Ala Gly Tyr Ala Arg Val Asp Pro Thr Val Ser His
                85                  90                  95
Cys Thr Gln Ser Val Leu Pro Ile Phe Trp Glu Pro Ser Ile Tyr Gln
            100                 105                 110
Thr Arg Lys Gln His Glu Phe Phe Glu Glu Ala Ser Ala Ala Gly Leu
        115                 120                 125
Val Tyr Gly Leu Thr Met Pro Leu His Gly Ala Arg Gly Glu Leu Gly
    130                 135                 140
Ala Leu Ser Leu Ser Val Glu Ala Glu Asn Arg Ala Glu Ala Asn Arg
145                 150                 155                 160
Phe Ile Glu Ser Val Leu Pro Thr Leu Trp Met Leu Lys Asp Tyr Ala
                165                 170                 175
Leu Gln Ser Gly Ala Gly Leu Ala Phe Glu His Pro Val Ser Lys Pro
            180                 185                 190
Val Val Leu Thr Ser Arg Glu Lys Glu Val Leu Gln Trp Cys Ala Ile
        195                 200                 205
Gly Lys Thr Ser Trp Glu Ile Ser Val Ile Cys Asn Cys Ser Glu Ala
    210                 215                 220
Asn Val Asn Phe His Met Gly Asn Ile Arg Arg Lys Phe Gly Val Thr
225                 230                 235                 240
Ser Arg Arg Val Ala Ala Ile Met Ala Val Asn Leu Gly Leu Ile Thr
                245                 250                 255
Leu Thr Cys Arg Ile Val Gln Val Tyr Ala Arg Lys Trp Phe Val Ile
            260                 265                 270
Val Glu Met Ser Asn Asp Asn Glu Val Pro Gly Ser Met Val Ile Val
        275                 280                 285
Ala Gln Gly Pro Asp Asp Gln Tyr Ala Tyr Glu Val Pro Pro Ile Asp
    290                 295                 300
Ser Ala Ala Val Ala Gly Asn Met Phe Gly Asp Leu Ile Gln Arg Glu
305                 310                 315                 320
Ile Tyr Leu Gln Lys Asn Ile Tyr Tyr Pro Val Arg Ser Ile Phe Glu
                325                 330                 335
Gln Gly Thr Lys Glu Lys Lys Glu Ile Asn Lys Val Ser Asp Gln
            340                 345                 350
Val Asp Gly Leu Leu Lys Gln Ile Thr Gln Gly Lys Arg Glu Ala Thr
        355                 360                 365
Arg Gln Glu Arg Val Asp Val Met Ser Ala Val Leu His Lys Met Glu
```

```
                    370                 375                 380
Ser Asp Leu Glu Gly Tyr Lys Lys Thr Phe Thr Lys Gly Pro Phe Ile
385                 390                 395                 400

Asp Tyr Glu Lys Gln Ser Ser Leu Ser Ile Tyr Glu Ala Trp Val Lys
                    405                 410                 415

Ile Trp Glu Lys Asn Ser Trp Glu Arg Lys Lys Tyr Pro Phe Gln
                    420                 425                 430

Gln Leu Val Arg Asp Glu Leu Glu Arg Ala Val Ala Tyr Tyr Lys Gln
                    435                 440                 445

Asp Ser Leu Ser Glu Ala Val Lys Val Leu Arg Gln Glu Leu Asn Lys
                    450                 455                 460

Gln Lys Ala Leu Lys Glu Lys Glu Asp Leu Ser Gln Leu Glu Arg Asp
465                 470                 475                 480

Tyr Arg Thr Arg Lys Ala Asn Leu Glu Met Lys Val Gln Ser Glu Leu
                    485                 490                 495

Asp Gln Ala Gly Ser Ala Leu Pro Pro Leu Val Ser Pro Thr Pro Glu
                    500                 505                 510

Gln Trp Leu Glu Arg Ala Thr Arg Leu Val Thr Gln Ala Ile Ala Asp
                    515                 520                 525

Lys Lys Gln Leu Gln Thr Thr Asn Asn Thr Leu Ile Lys Asn Ser Pro
                    530                 535                 540

Thr Pro Leu Glu Lys Gln Lys Ala Ile Tyr Asn Gly Glu Leu Leu Val
545                 550                 555                 560

Asp Glu Ile Ala Ser Leu Gln Ala Arg Leu Val Lys Leu Asn Ala Glu
                    565                 570                 575

Thr Thr Arg Arg Arg Thr Glu Ala Glu Arg Lys Ala Ala Glu Glu Gln
                    580                 585                 590

Ala Leu Gln Asp Ala Ile Lys Phe Thr Ala Asp Phe Tyr Lys Glu Val
                    595                 600                 605

Thr Glu Lys Phe Gly Ala Arg Thr Ser Glu Met Ala Arg Gln Leu Ala
                    610                 615                 620

Glu Gly Ala Arg Gly Lys Asn Ile Arg Ser Ser Ala Glu Ala Ile Lys
625                 630                 635                 640

Ser Phe Glu Lys His Lys Asp Ala Leu Asn Lys Lys Leu Ser Leu Lys
                    645                 650                 655

Asp Arg Gln Ala Ile Ala Lys Ala Phe Asp Ser Leu Asp Lys Gln Met
                    660                 665                 670

Met Ala Lys Ser Leu Glu Lys Phe Ser Lys Gly Phe Gly Val Val Gly
                    675                 680                 685

Lys Ala Ile Asp Ala Ala Ser Leu Tyr Gln Glu Phe Lys Ile Ser Thr
690                 695                 700

Glu Thr Gly Asp Trp Lys Pro Phe Phe Val Lys Ile Glu Thr Leu Ala
705                 710                 715                 720

Ala Gly Ala Ala Ala Ser Trp Leu Val Gly Ile Ala Phe Ala Thr Ala
                    725                 730                 735

Thr Ala Thr Pro Ile Gly Ile Leu Gly Phe Ala Leu Val Met Ala Val
                    740                 745                 750

Thr Gly Ala Met Ile Asp Glu Asp Leu Leu Glu Lys Ala Asn Asn Leu
                    755                 760                 765

Val Ile Ser Ile Thr Cys Arg Ile Val Gln Val Tyr Ala Arg Lys Trp
770                 775                 780

Phe Val Ile Val Glu Met Lys Lys Ile Thr Gly Ile Ile Leu Leu Leu
785                 790                 795                 800
```

-continued

```
Leu Ala Ala Ile Ile Leu Ala Ala Cys Gln Ala Asn Tyr Ile Arg Asp
                805                 810                 815
Val Gln Gly Gly Thr Val Ser Pro Ser Ser Thr Ala Glu Leu Thr Gly
            820                 825                 830
Val Glu Thr Gln
        835
```

ISOLATED NUCLEOTIDE MOLECULE AND METHOD OF SENSING AND KILLING OF PATHOGENIC MICROORGANISM

CROSS-REFERENCE TO RELATED APPLICATION

This application claims the benefit of priority of U.S. provisional patent application No. 61/529,417, filed Aug. 31, 2011, the contents of it being hereby incorporated by reference in its entirety for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_431a_SEQUENCE_LISTING.txt. The text file is 24 KB, was created on Oct. 24, 2012, and is being submitted electronically via EFS-Web.

TECHNICAL FIELD

Various embodiments relate to the field of an engineered microbe that can sense and eradicate a pathogenic microorganism, in particular, *Pseudomonas aeruginosa*.

BACKGROUND

Synthetic biology aims to engineer genetically modified biological systems that perform novel functions that do not exist in nature, with reusable, standard interchangeable biological parts. The use of these standard biological parts enables the exploitation of common engineering principles such as standardization, decoupling, and abstraction for synthetic biology. With this engineering framework in place, synthetic biology has the potential to make the construction of novel biological systems a predictable, reliable, systematic process. While the development of most synthetic biological systems remains largely ad hoc, recent efforts to implement an engineering framework in synthetic biology have provided long-awaited evidences that engineering principles can facilitate the construction of novel biological systems. Synthetic biology has demonstrated that its framework can be applied to a wide range of areas such as energy, environment, and health care. For example, biological systems have been constructed to produce drugs and biofuels, to degrade contaminants in water, and to kill cancer cells.

Despite these advances, synthetic biology has not yet been exploited to develop new strategies for tackling infectious disease, a leading cause of death worldwide, especially in poor countries. Given the stalled development of new antibiotics and the increasing emergence of multidrug-resistant pathogens, using synthetic biology to design new treatment regimens for infectious disease could address an urgent need.

*Pseudomonas aeruginosa* (or often referred to as *P. aeruginosa*) colonizes the respiratory and gastrointestinal tract, and causes life-threatening infections to patients with immunodeficiency such as cystic fibrosis and cancer. Despite a wide range of antibiotics available in the market, *P. aeruginosa* is still among the leading causes of nosocomial infection primarily because it is intrinsically resistant to many antibiotics and antimicrobials, in part because of its effective efflux systems. Contemporary treatments against *P. aeruginosa* infection include antibiotic chemotherapy and bacteriophage therapy. In antibiotic chemotherapy, a combinatorial treatment involving multiple antimicrobial agents is usually preferred over monotherapy due to the rapid acquisition of drug tolerance in *P. aeruginosa*. This approach, however, promotes unspecific killing of bacteria and upsets a healthy human microbiome. Phage therapy involves strain-specific bacteriophages that invade and destroy the cellular integrity of pathogens. The therapeutic potential of employing virus in bacterial infection, however, is limited, as a directed treatment cannot be re-employed after the infected host develops specific antibodies against the introduced virus.

Thus, there is need in the art for novel, unconventional antimicrobial strategies that do not entirely rely on current antibiotics that address the problems mentioned above, especially in combating *P. aeruginosa* infections.

SUMMARY OF THE INVENTION

In a first aspect of the present invention, an isolated nucleic acid molecule is provided. The isolated nucleic acid molecule comprises a first nucleotide sequence encoding a protein that detects the presence, amount or both of a pathogenic microorganism by forming a complex with a protein produced by said pathogenic microorganism, a second nucleotide sequence encoding an antimicrobial peptide, wherein the antimicrobial peptide is effective against the pathogenic microorganism detected by the protein encoded by the first nucleotide sequence, wherein the second nucleotide sequence is under control of a promoter that is induced by the complex of the protein encoded by the first nucleotide sequence and the protein produced by said pathogenic microorganism.

In a second aspect, a recombinant microorganism is provided. The recombinant microorganism comprises the isolated nucleic acid molecule comprising a first nucleotide sequence encoding a protein that detects the presence, amount or both of a pathogenic microorganism by forming a complex with a protein produced by said pathogenic microorganism, a second nucleotide sequence encoding an antimicrobial peptide, wherein the antimicrobial peptide is effective against the pathogenic microorganism detected by the protein encoded by the first nucleotide sequence, wherein the second nucleotide sequence is under control of a promoter that is induced by the complex of the protein encoded by the first nucleotide sequence and the protein produced by said pathogenic microorganism. In one embodiment, the isolated nucleic acid is comprised in a vector.

In a further aspect, the present invention relates to a method of sensing and killing pathogenic microorganisms. The method comprises contacting a recombinant microorganism with the pathogenic microorganism. The recombinant microorganism comprises an isolated nucleic acid molecule including a first nucleotide sequence encoding a protein that detects the presence, amount or both of a pathogenic microorganism by forming a complex with a protein produced by said pathogenic microorganism, a second nucleotide sequence encoding an antimicrobial peptide, wherein the antimicrobial peptide is effective against the pathogenic microorganism detected by the protein encoded by the first nucleotide sequence, wherein the second nucleotide sequence is under control of a promoter that is induced by the complex of the protein encoded by the first nucleotide sequence and the protein produced by the pathogenic microorganism.

BRIEF DESCRIPTION OF THE DRAWINGS

The invention will be better understood with reference to the detailed description when considered in conjunction with non-limiting examples and the accompanying drawings, in which:

FIG. 2 shows the characterization of sensing device coupled with GFP reporter.

FIG. 3 shows the characterization of a lysis device using $3OC_{12}HSL$.

FIG. 4 shows the characterization of the lysis device in the final system using $3OC_{12}HSL$.

FIG. 5 shows the inhibition of *P. aeruginosa* by the engineered *E. coli* induced with native $3OC_{12}HSL$ produced by *P. aeruginosa*. FIG. 5D shows the percentage survival of *P. aeruginosa* carrying chloramphenicol-resistant plasmid in mixed culture with the engineered *E. coli*. *Pseudomonas* in the mixed culture was quantified by viable cell count using chloramphenicol selection. It was observed that the engineered *E. coli* according to various embodiments inhibited the growth of *Pseudomonas* by 99%. In contrast, inhibition was less observed in *Pseudomonas* co-cultured with incomplete *E. coli* systems missing either the pyocin S5 killing device or E7 lysis device. Error bar represents the standard deviation of three replicates.

FIG. 6 shows biofilm inhibition assay with engineered *E. coli*.

FIG. 7 shows the plasmid map of the engineered system/devices in pSB1A2 vector. FIG. 7D shows a sensing device with pyocin S5, pTetR-LasR-pLuxR-S5. This construct was used as a control to compare the efficiency of lysis device in mediating protein release.

FIG. 8 shows inhibition of *P. aeruginosa* by the engineered *E. coli* induced with $3OC_{12}HSL$.

FIGS. 9A and 9B show a table that summarizes all plasmids, Biobrick parts, and devices used in the Examples.

DETAILED DESCRIPTION OF THE INVENTION

Figure 1:
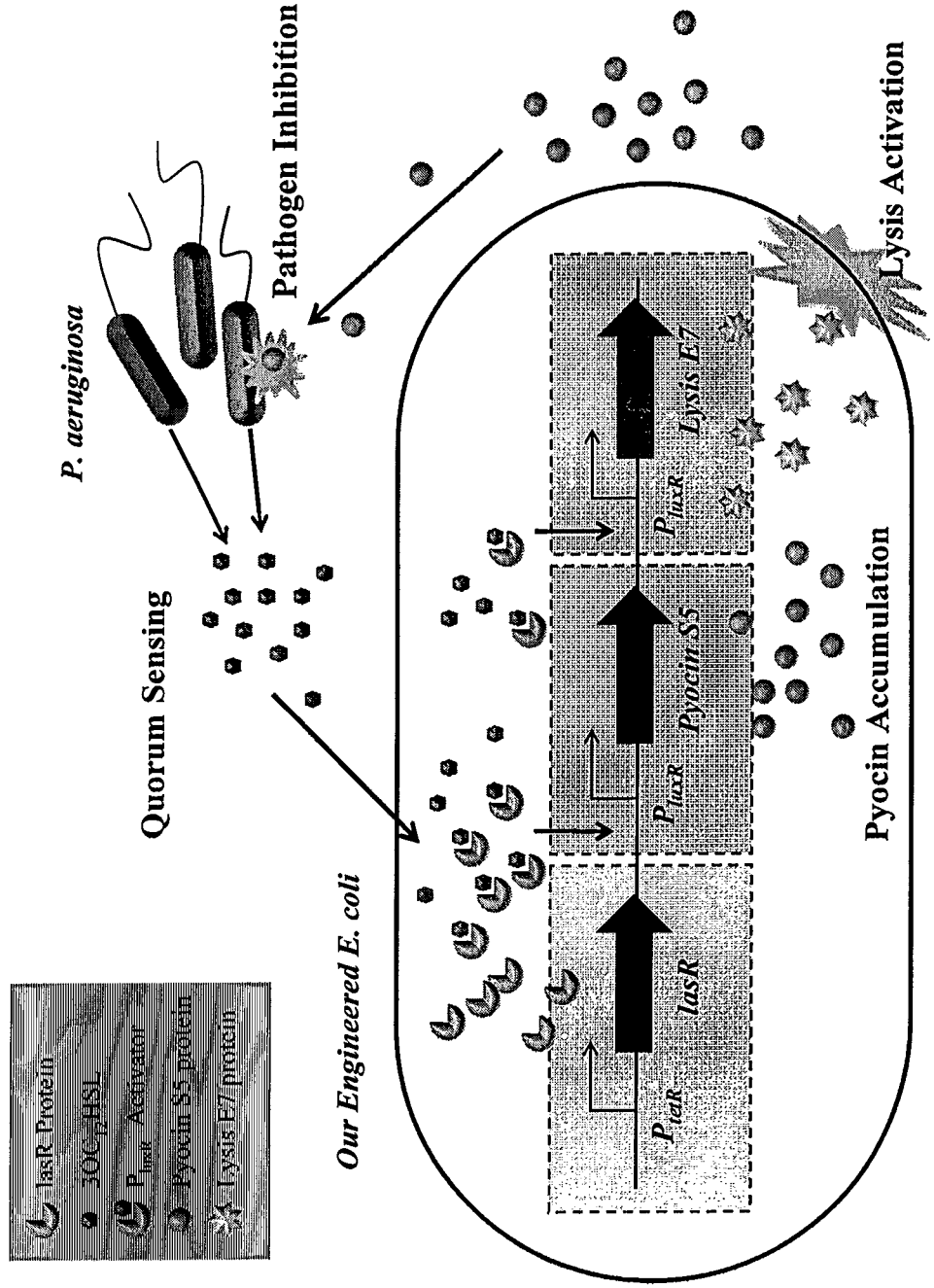
FIG. 1 shows a schematic overview of 'Pathogen Sensing and Killing' system, according to various embodiments. The sensing device was designed based on the Type I quorum sensing mechanism of P. aeruginosa. The tetR promoter ($P_{tetR}$), which is constitutively on, produces a transcriptional factor, LasR, that binds to AHL $3OC_{12}HSL$. The luxR promoter ($P_{luxR}$), to which LasR-$3OC_{12}HSL$ activator complex reportedly binds, was adopted as the inducible promoter in the sensing device. Next, the formation of the LasR-$3OC_{12}HSL$ complex, which binds to the luxR promoter, activates the killing and lysing devices, leading to the production of pyocin S5 and lysis E7 proteins within the *Escherichia coli* chassis. Upon reaching a threshold concentration, the lysis E7 protein perforates membrane of the *E. coli* host and releases the accumulated pyocin S5. Pyocin S5, which is a soluble protein, then diffuses toward the target pathogen and damages its cellular integrity, thereby killing it.

The following detailed description refers to the accompanying drawings that show, by way of illustration, specific details and embodiments in which the invention may be practised. These embodiments are described in sufficient detail to enable those skilled in the art to practise the invention.

Various embodiments provide a novel antimicrobial strategy based on an engineered microbial system using the synthetic biology framework.

Various embodiments may provide a genetic system that was designed and constructed based on standardization, decoupling, and abstraction that allows sensing and killing of *P. aeruginosa*, a human pathogen, in a non-pathogenic chassis, *E. coli*.

Various embodiments may also provide an engineering microbe to sense and eradicate *P. aeruginosa*, a human pathogen.

The biological parts of the devices may be designed and synthesized in compliance with the BioBrick assembly standards. Each of the biological devices may be characterized to understand its behaviour, and the correlation between the input and output of the biological device may be studied in detail.

In a first aspect, an isolated nucleic acid molecule is provided. The isolated nucleic acid molecule comprises a first nucleotide sequence encoding a protein that detects the presence, amount or both of a pathogenic microorganism by forming a complex with a protein produced by said pathogenic microorganism, and a second nucleotide sequence encoding an antimicrobial peptide, wherein the antimicrobial peptide is effective against the pathogenic microorganism detected by the protein encoded by the first nucleotide sequence, wherein the second nucleotide sequence is under control of a promoter that is induced by the complex of the protein encoded by the first nucleotide sequence and the protein produced by said pathogenic microorganism.

As used herein in connection with a nucleic acid molecule, the term "isolated" refers to a nucleic acid molecule that is substantially free of other cellular material or components or culture medium, in particular when produced by recombinant techniques, or substantially free of chemical precursors and/or other chemical agents when chemically synthesized.

The term "nucleic acid molecule", as used herein, includes all forms of nucleic acids and includes DNA and RNA, in particular DNA, and may be single or double-stranded. Besides the nucleotide sequence encoding the protein for detection of the pathogenic microorganism, the nucleic acid molecule may comprise non-coding regions, such as sequences that control its expression, including, but not limited to promoters, enhancers, transcription factor binding sites, restriction enzyme binding sites, methylation sites, and the like.

The term "peptide" generally refers to polymers of amino acids and includes dipeptides, oligopeptides and polypeptides. In various embodiments of the invention, the antimicrobial peptides consist of 10 to 100 amino acids. In this context, "antimicrobial" means that the peptide inhibits the growth of or kills microorganisms, as defined below.

The term "pathogenic microorganism" includes bacteria, viruses, protozoa and fungi that can cause diseases or disorders in other, preferably eukaryotic, organisms, such as mammals, including humans.

For example, the pathogenic microorganism may be *P. aeruginosa*. In other examples, pathogenic microorganism may include but is not limited to *Clostridium difficile, E. coli, Helicobacter pylori, Salmonella* spec., *Vibrio cholera* and *Yersinia* spec.

The term "promoter" relates to transcriptional regulatory sequences that promote expression of a gene. Generally, numerous promoters as well as their use in recombinant systems are known to those skilled in the art. A promoter is usually but not necessarily, positioned upstream, or 5', of a structural gene to be expressed.

The term "complex", as used herein, relates to a complex of two or more proteins that are, usually non-covalently bound to each other. The complex may be a specific complex, i.e. the proteins of the complex specifically bind to each other, meaning that they preferentially bind to each other over other proteins that may be present in a cellular environment. The affinity of the complex proteins to each other should be high enough to allow complex formation. In various embodiments, the dissociation constant of the complex, $K_d$, is at least $10^{-6}$ M. In this context, specific binding may mean that the complex partners bind to each other with an at least 10 fold, at least 100-fold, or at least 1000-fold higher affinity compared to other proteins.

In one embodiment, the first nucleotide sequence may be under control of a constitutively active promoter. In various embodiments, the constitutive promoters which regulate the first nucleotide sequence may include any synthetic $\sigma^{70}$ or $\sigma^S$ promoters (e.g., synthetic $\sigma^{70}$ promoters with define −10 box TATAAT and −35 box TTGACA).

As used herein, by "constitutively active promoter" it is meant that a promoter that is continuously active, i.e. an operably linked nucleic acid sequence is continuously expressed, without being subject to regulation by external signals or inducer molecules. The term "promoter" is as defined above. Examples of suitable constitutive promoters may include those of viral origin, e.g., SV40 (early and late promoters), adenovirus major late promoter, Rous sarcoma virus (RSV) promoter, cytomegalovirus (CMV) immediate-early promoter, and major-intermediate-early (MIE) promoters. These promoters are useful because of their strength, constitutive expression and the ability to be expressed in varied cell lines.

In various embodiments, the protein encoded by the first nucleotide sequence may specifically detect acyl homoserine lactones (AHL).

The term "acyl homoserine lactones (AHL)" refers to intracellular signal molecules produced by different microorganisms, including *P. aeruginosa*, and may be released outside of the bacterial cell, involved in quorum-sensing. For example, in the context of *P. aeruginosa*, the quorum-sensing molecule released may include AHL-dependent signalling molecules, such as N-butanoyl-l-homoserine lactone ($C_4HSL$) and N-3-oxododecanoyl homoserine lactone ($3OC_{12}HSL$) and/or AHL-independent quinolone-signalling molecule, e.g., 2-heptyl-3-hydroxy-4(1H)-quinolone.

In various embodiments, the protein encoded by the first nucleotide sequence may be a transcription factor.

In various embodiments, the transcription factor may be the protein LasR produced by the transcription and subsequent translation of the $P_{tetR}$ gene. Said LasR protein specifically interacts with microbial AHLs by forming a non-covalent complex therewith. Upon forming a complex with the AHL, e.g. those produced by *P. aeruginosa*, the complex then may bind to the transcription initiation site, i.e., the promoter, for example $P_{luxR}$, controlling expression of the antimicrobial peptide and optionally the lysis protein. The genes encoding the antimicrobial peptide and lysis protein may be the pyocin and lysis E7 genes, respectively.

In one embodiment, the protein encoded by the first nucleotide sequence may be the transcription factor LasR that binds to the AHL N-3-oxododecanoyl homoserine lactone ($3OC_{12}HSL$). In an example, another combination of quorum sensing system that may be applied to detect *P. aeruginosa* may include the transcription factor RhlR that recognizes and binds the AHL N-butanoyl-l-homoserine lactone ($C_4HSL$).

In various embodiments, the first nucleotide sequence may have the nucleotide sequence set forth in SEQ ID NO:1. For example, SEQ ID NO:1 may be based on LasR gene (UniProt: PSPA7_3898).

In some examples, the first nucleotide sequence may include $P_{tetR}$-LasR (SEQ ID NO:5). For example, the $P_{tetR}$ may be obtained from an *E. coli* plasmid cloning vector containing the p15A origin of replication (1-4) (GenBank: pACYC184).

In various embodiments, the inducible promoter of the second nucleotide sequence may be the luxR promoter that is bound and induced by a complex of LasR and $3OC_{12}HSL$.

In the context of various embodiments, the term "inducible promoter" means a promoter that is not constitutively active, but rather is activated by external factors, such as binding partners, and thus able to regulate the amount and the timing of protein expression. The term "promoter" is as defined above. Besides the luxR promoter mentioned above, other inducible promoters that may be used to regulate the expression of the second nucleotide sequence include natural or synthetic luxR promoter analogues e.g., promoters of aprA, rhlI, rhlR, lasA, lasB, lasI and toxA. Herein, the phrase "synthetic promoter" refers to promoter variants generated by mutagenesis of the luxR promoter or its analogues, all of which are activated when bound to a complex of LasR and $3OC_{12}HSL$.

In various embodiments, the protein encoded by the second nucleotide sequence may be a bacteriocin.

The term "bacteriocin" refers to proteinaceous toxins produced by bacteria to inhibit the growth of similar or closely related bacterial strain(s). Various embodiments of the invention employ bacteriocins, ribosomally synthesized antimicrobial peptides. Bacteriocins are specific and effective against closely related species, and thus have garnered attention as a new generation antibacterial agent. For example, the bacteriocin may be a pyocin. Other examples of bacteriocins include colicin (e.g., against *E. coli*), lacticin 3147 (e.g., against *Clostridium difficile*) and vibriocin (e.g., against *Vibrio cholera*).

Pyocins are narrow-spectrum bacteriocins produced by *P. aeruginosa*. Contrary to traditional antibiotics, the acquisition of pyocin resistance by lateral gene transfer between bacteria has not yet been encountered, supporting the use of pyocins in targeting *P. aeruginosa* infection. Pyocins are classified into three types: R, F, and S. R and F type pyocins may be synthesized by 90% of all *P. aeruginosa* strains and S type by 70%. More specifically, examples of pyocin may include S-type pyocins (e.g., S1, S2, S3, S4, AP41), R-type pyocins (e.g., R1, R2, R3) and F type pyocins (e.g., F1, F2, F3). The soluble S type pyocin, hereby named as Pyocin S5 (which may be interchangeably referred to "S5 pyocin") exhibits strong bactericidal activity against *P. aeruginosa* clinical isolates through membrane damage but is ineffective against *E. coli*.

In one embodiment, the pyocin may be pyocin S5.

In various embodiments, the inducible promoter of the second nucleotide sequence may be the luxR promoter that may be bound and induced by a complex of LasR and $3OC_{12}HSL$.

The second nucleotide sequence together with the inducible promoter may have the nucleotide sequence set forth in SEQ ID NO:2. For example, SEQ ID NO:2 may be $P_{luxR}$-pyocin S5. The inducible promoter may be obtained from a *Vibrio fischeri* regulatory protein LuxR (luxR) gene (GenBank: AF170104.1) and the second nucleotide sequence may be pyocin S5 obtained from *P. aeruginosa* (strain ATCC 15692/PAO1/1C/PRS 101/LMG 12228) (UniProtKB/TrEMBL: Q9I4Y4_PSEAE).

In various embodiments, the protein encoded by the first nucleotide sequence, the protein encoded by the second nucleotide sequence or both may be specific for a pathogenic microorganism.

In various embodiments, the nucleic acid molecule may further comprise a third nucleotide sequence encoding a protein that may be capable of lysing a cell hosting the isolated nucleic acid molecule, wherein said third nucleotide sequence may be under control of a promoter that may be induced by the complex of the protein encoded by the first nucleotide sequence and the protein produced by said pathogenic microorganism.

In the context of various embodiments, the term "lysing" refers to the perforation of the cell membrane and the subsequent release of the cytoplasmic components (i.e. components within the cell).

The protein encoded by the third nucleotide sequence may be a lysis protein that lyses the cell membrane of a cell hosting the nucleic acid molecule, for example an *E. coli* host cell.

The protein encoded by the third nucleotide sequence may be the E7 lysis protein. In other embodiments, *E. coli* host lysis may be mediated by any lytic systems utilizing phage holin and endolysin lysis proteins, or bacteriocin release proteins of cloacin DF13, colicin E1, E3, A and D.

In various embodiments, the third nucleotide sequence together with the inducible promoter may have the nucleotide sequence set forth in SEQ ID NO:3.

For example, SEQ ID NO:3 may be $P_{luxR}$-E7 lysis. The inducible promoter may be as defined above. The third nucleotide sequence may be E7 lysis obtained from *Human papillomavirus* type 16 (VE7_HPV16) (UniProtKB/Swiss-Prot: Q03709).

Various embodiments may provide a system designed to (i) detect AHLs produced by *P. aeruginosa*; (ii) produce pyocin S5 upon the detection; and (iii) lyse the *E. coli* cells by E7 lysis protein so that the produced pyocin S5 is released from the cells, leading to the killing of *P. aeruginosa*. The engineered *E. coli* may effectively sense and kill *P. aeruginosa*; thereby providing a novel synthetic biology-based antimicrobial strategy that may be applied to eradicating other infectious pathogens.

The quorum sensing mechanisms of *P. aeruginosa* may enable the engineered microbes to produce pyocin S5 only in response to the presence of *P. aeruginosa*. The term "quorum sensing" as used herein refers to the intercellular communication between bacteria. This sensing mechanism is mediated by various diffusible, chemical signals known as autoinducers that are produced by the synthase genes of the bacteria. The extracellular concentration of signaling molecules increases as a function of cell density and is permeable to cell membrane. Upon attaining a threshold concentration of the chemical signals, the quorum sensing cascade is activated to elicit expressions or repressions of multiple genes, including those that are functional for production of autoinducers such as acyl homoserine lactones (AHLs). This organic signaling cascade therefore regulates a myriad of physiological activities such as cell motility, virulence, biofilm formation and growth. Although similar production mechanisms are present in some Gram-negative bacteria, each synthase homolog producing AHLs differs in either length or functional groups (e.g., hydroxyl and carbonyl groups) on the acyl side chain. Thus, with each bacterium possessing disparate synthase sequence, a high level of specificity can be achieved during intercellular quorum communication.

In various embodiments, the E7 lysis protein may be utilised to lyse the *E. coli* chassis to enable an effective release of pyocin S5. The E7 lysis protein is a key component of the SOS response system in colicin-producing cells and functions to export bacteriocins into the extracellular space under stressful environmental conditions. The E7 lysis protein may be effective in causing inner membrane damage and maybe associated with the activation of outer membrane phospholipase A for outer membrane modification. In addition to being specific to *E. coli*, the E7 lysis protein is small at 47 amino acids and may be easily utilized as a modular part in the assembly of novel genetic circuits.

Based on the above mentioned system, the isolated nucleic acid molecule in accordance to various embodiments may comprise the nucleotide sequence set forth in SEQ ID NO:4. For example, SEQ ID NO:4 may be LasR-$P_{luxR}$-pyocin S5-$P_{luxR}$-E7 lysis.

In some examples, the isolated nucleic acid molecule may include $P_{tetR}$-LasR-$P_{luxR}$-pyocin S5-$P_{luxR}$-E7 lysis (SEQ ID NO:6).

In various embodiments, the isolated nucleic acid molecule may be comprised in a vector.

As used herein, the term "vector" relates to any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and the like, that are "episomes", that is, that replicate autonomously or may integrate into a chromosome of a host cell. For example, a vector may also be a naked RNA polynucleotide, a naked DNA polynucleotide, a polynucleotide composing both DNA and RNA, a liposome-conjugated DNA, or the like, that are not episomal in nature, or it may be an organism which comprises one or more of the above polynucleotide constructs such as an *agrobacterium*.

In a second aspect, a recombinant microorganism is provided. The recombinant microorganism comprises the isolated nucleic acid molecule as defined above.

The term "recombinant microorganism" refers to a microorganism that has been genetically modified to express or over-express endogenous polynucleotides, or to express non-endogenous sequences, such as those included in a vector, or which have a reduction in expression of an endogenous gene. The polynucleotide generally encodes a target enzyme involved in a metabolic pathway for producing a desired metabolite.

The recombinant microorganism may be interchangeably referred to as a microbe, an engineered microbe, an engineering microbe, a sensing device or an engineered biological system.

In various embodiments, the recombinant microorganism may be *E. coli*.

In another aspect, a method of sensing and killing pathogenic microorganisms is provided. The method comprises contacting the recombinant microorganism as defined above with the pathogenic microorganism.

In various embodiments, the method may be a method of sensing and killing pathogenic microorganisms in a subject. The method may comprise administering the recombinant microorganism as defined above to the subject.

In various embodiments, the pathogenic microorganism may be a human pathogen. The term "human pathogen" may generally refer to any pathogenic microorganism that may cause disease in or death to a human being.

For example, the pathogenic microorganism may be *P. aeruginosa*. The term "pathogenic microorganism" may be as defined above.

In order that the invention may be readily understood and put into practical effect, particular embodiments will now be described by way of the following non-limiting examples.

Materials and Methods
Strains and Media

Figure 9A:
Figure 9A:
Figure 9A:
Figure 9A:
Figure 9A:
Figure 9A:
Figure 9A:
Figure 9A:
Figure 9A:

All cells involved in cloning and characterization are *E. coli* TOP10 (Invitrogen) unless otherwise stated. Commercial Luria-Bertani (LB) and Muller Hinton (MHB) were used as the medium for cloning and inhibition studies unless otherwise stated. Supplemented M9 (M9 salts, 1 mM thiamine hydrochloride, 0.4% glycerol, 0.2% casamino acids, 0.1 M MgSO$_4$, 0.5 M CaCl$_2$) was used as the medium for the characterization. Ampicillin (100 μg/ml) was added to the culture media for antibiotic selection where appropriate. Homoserine lactone (3OC$_{12}$HSL; Sigma Aldrich) was used for characterization experiments. All restriction and ligation enzymes were purchased from New England Biolabs (NEB). FIGS. 9A and 9B summarize all plasmids, Biobrick parts, and devices used in this example. The part number, functional description and symbol used are listed for each component. Descriptions of all BBa parts may be found in the Registry of Standard Biological Parts while the rest are explained herein.

Figure 7A:
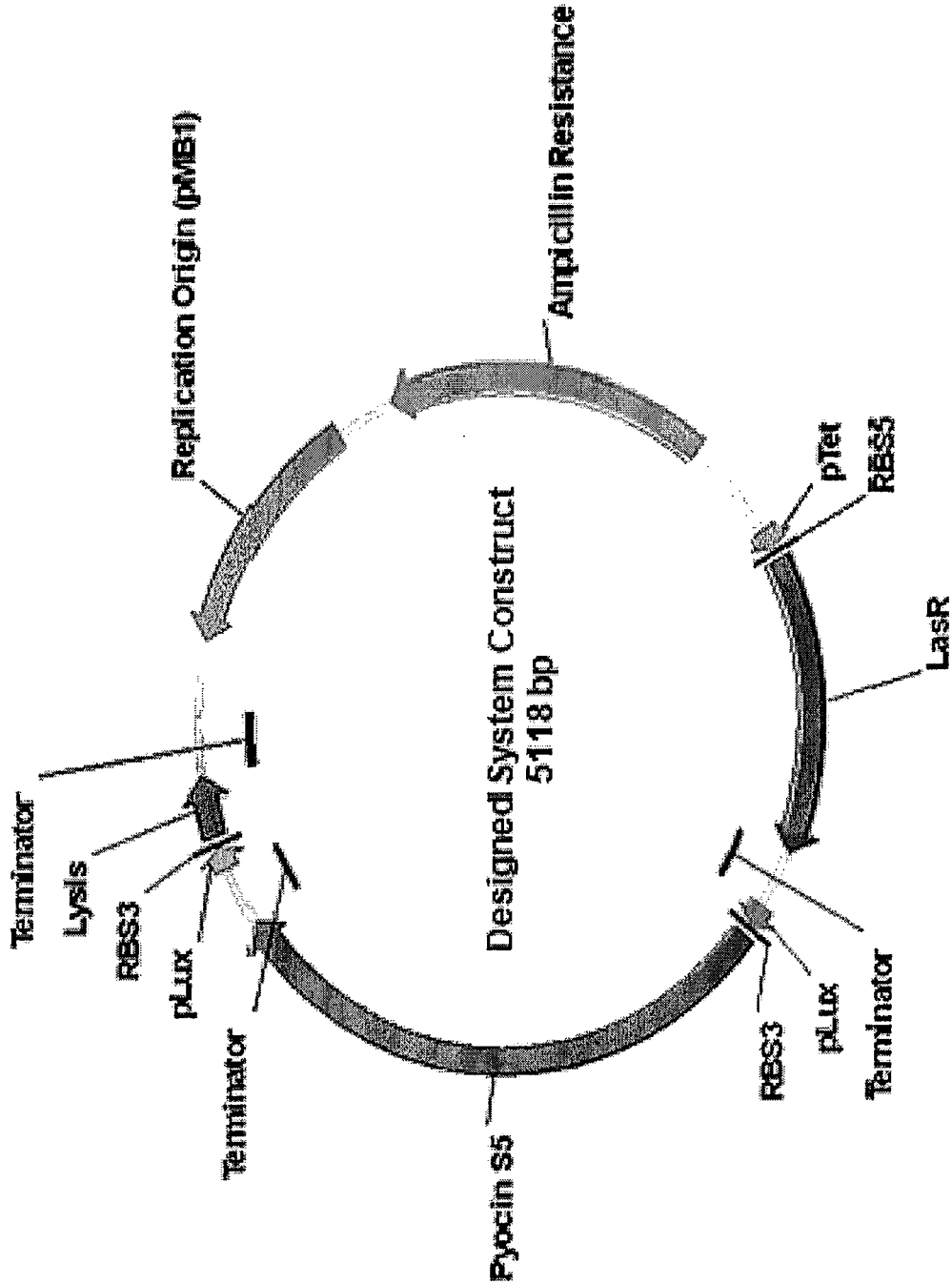
FIG. 7A shows the final engineered system, pTetR-LasR-pLuxR-S5-pLuxR-E7. The system recognizes input chemical signals from *P. aeruginosa* and produces S5 pyocin and E7 lysis proteins.

Genetic mapping of representative engineered constructs is illustrated in FIG. 7.

System Assembly

The genetic constructs developed in this example were assembled using standard synthetic biology protocols. Briefly, for front insertion of Biobrick parts, purified insert and vector plasmids were digested with EcoRI/SpeI and EcoRI/XbaI respectively. For back insertion to upstream vector, the insert and vector plasmids were digested with XbaI/PstI and SpeI/PstI in that order. Digested fragments were separated by DNA gel electrophoresis and ligated with NEB Quick Ligase in accordance with the manufacturer's instructions. Plasmids from chemically transformed cells were purified by affinity columns and verified by DNA sequencing.

Characterization of pTetR-LasR pLuxR-GFP with 3OC$_{12}$HSL

Single colonies of pTetR-LasR-pLuxR-GFP (Top10) were each inoculated into 5 ml of pre-warmed supplemented M9 ampicillin for overnight culture in a shaking incubator at 37° C. After overnight growth, the cultures were diluted to OD$_{600}$ of 0.002 and allowed to incubate further to OD$_{600}$ of 0.5 or 5.0E7 cfu/ml under the same condition. Cultures were then transferred into a transparent, flat-bottom 96-well plate in triplicate aliquots of 200 μl for induction with 3OC$_{12}$HSL at varying molar concentrations (0, 5.0E-10, 1.0E-9, 5.0E-9, 1.0E-8, 5.0E-8, 1.0E-7, 2.5E 7, 5.0E-7, 1.0E-6, 5.0E-6, 1.0E-6, 5.0E-5, and 1.0E-4 M). The plate was incubated at 37° C. with rapid shaking in a microplate reader (Biotek) and assayed for green fluorescence. Time-series fluorescence and OD$_{600}$ data were obtained at intervals of 10 mins for a total run time of 3 hrs. The measurement was zeroed with supplemented M9 to remove background fluorescence and OD$_{600}$. A relative GFP production rate was derived as a ratio of background subtracted green fluorescence to OD$_{600}$ value. A time-averaged GFP synthesis rate was obtained by averaging the relative GFP production rates between 20 and 80 mins after induction with 3OC$_{12}$HSL. The measured data were fitted using an empirical mathematical model (Hill equation) as seen in Equation (1):

$$Y = A + (B[C_{12}]^n / (C^n + [C_{12}]^n)) \quad (1)$$

Equation (1) models GFP synthesis rate (y) as a function of input concentration of 3OC$_{12}$HSL ([C12]). The four parameters (A, B, C, n) were estimated to obtain the best fit curve by performing a non-linear curve fitting using the experimental results. This curve fitting was performed using MATLAB Curve Fitting Toolbox (The Mathworks, Natwick, Mass., USA).

Detection of the Native Autoinducer Produced by *P. aeruginosa*

GFP production rates induced by 3OC$_{12}$HSL natively produced from *P. aeruginosa* were measured with pTetR-LasR-pLuxR quorum sensor as described above. Briefly, overnight cultures of pTetR-LasR-pLuxR-GFP (Top10) were diluted in Supplemented M9. Diluted *Pseudomonas* cultures were grown to a late logarithmic phase and filtered with a filter membrane (0.22 μm). Sterile filtrates containing 3OC$_{12}$HSL were mixed with pTetR-LasR-pLuxR-GFP culture to activate GFP production. The resultant mixtures were transferred into a transparent, flat-bottom 96-well plate in triplicate aliquots of 200 μl to be assayed for GFP production rates in a microplate reader (Biotek) at 37° C. with rapid shaking. The rates obtained were then compared with the Hill function mathematical model as in Equation (1) using 3OC$_{12}$HSL to estimate the native 3OC$_{12}$HSL concentration from *P. aeruginosa* ln 7.

Characterization of Lysis Device with 3OC$_{12}$HSL

Overnight cultures of pTetR-LasR-pLuxR-E7 (Top10) were diluted in supplemented M9 and harvested at an OD$_{600}$ of 0.5. The resultant cultures were transferred into a transparent, flat-bottom 96-well plate in triplicate aliquots of 200 μl for induction with 3OC$_{12}$HSL at varying concentrations (i.e., 0, 1.0E-8, 1.0E-6, and 1.0E-4 M). The plate was incubated at 37° C. with rapid shaking in a microplate reader (Biotek) and assayed for cell turbidity. Time-series absorbance at OD$_{600}$ was obtained at intervals of 10 mins for a total run time of 6 hrs. The result was zeroed with supplemented M9 to remove background absorbance.

FESEM Assay

To examine the effect of E7 lysis protein on cell morphology, reinoculated cultures of pTetR-LasR-pLuxR-E7 (Top10) and pTetR-LasR-pLuxR-S5-pLuxR-E7 (Top10) were induced with 1.0E-6 M 3OC$_{12}$HSL at OD$_{600}$ of 0.5 and cultured for 2 hrs. Cell pellets collected after centrifugation at 4000 rpm for 15 mins were washed with 0.1 M sodium cacodylate (pH 7.4) three times before fixation with 2.5% glutaraldehyde in 0.1 M sodium cacodylate for 2 hrs of incubation at 4° C. Cell pellets were further washed three times with sodium cacodylate after fixation and resuspended in 0.1 M sodium cacodylate (volume depends on cell amount). In all, 2 μl of sample was loaded onto PEI-coated silicon slide followed by incubation at 25° C. for 30 mins. The loaded silicon slide was fixed in 1% osmium tetraoxide in 0.1 M sodium cacodylate at 25° C. for 90 mins. Silicon slide was then dehydrated in serial concentrations of absolute ethanol (37, 67, 95% and three times of 100%) for 15 mins each before drying in a vacuum evaporator overnight. Coating of silicon slide was performed with 20 nm of gold-palladium alloy (60:40) and examined using a field-emission scanning electron microscope (JSM-6700F FESEM) at 10 kV.

Characterization of Lysis Device by Protein Release in Engineered *E. coli*

To characterize the efficiency of the lysis device in mediating pyocin release, pTetR-LasR-pLuxR-S5-pLuxR-E7 and pTetR-LasR-pLuxR-S5 plasmids were first labeled with hexa-histidine tags on the 3' terminus of S5 gene with pfu polymerase (Promega) and transformed into *E. coli* Top10. Overnight cultures of the His-tag version of pTetR-LasR-pLuxR-S5-pLuxR-E7 and pTetR-LasR-pLuxR-S5 were then diluted in LB and harvested at an OD$_{600}$ of 0.7. The collected cultures were induced with 1.0E-6 M 3OC$_{12}$HSL and incubated for 6 hrs in a shaking flask culture set at 37° C. and 170 rpm. At regular intervals of 2 hrs, cell cultures were drawn and filter sterilized (0.22 μm). The filtered cultures were mixed with 1/10 volume of 100% (w/v) trichloroacetic acid (Sigma-Aldrich) and incubated on ice for 1 hr to allow protein precipitation, before being washed with an equal volume of acetone. Precipitated proteins were reconstituted in 1 ml of reconstitution solvent (1×PBS, 30 mM imidazole and 4 M urea; pH 6.0) and purified by immobilized metal affinity chromatography using Vivapure miniprep MC (Sartorius Stedim Biotech GmbH) in accordance to the manufacturer's instruction. Finally, purified pyocin proteins were analyzed by SDS-PAGE and Bradford assay.

Overlay Inhibition Assay with $3OC_{12}HSL$ and the Final System

Overnight cultures of pTetR-LasR-pLuxR-S5-pLuxR-E7 (Top10), P. aeruginosa ln 7 and PAO1 were diluted in LB and harvested at $OD_{600}$ of 0.7 and 0.2 separately. Collected cultures of pTetR-LasRpLuxR-S5-pLuxR-E7 (Top10) were induced with varying molar concentrations of $3OC_{12}HSL$ (0, 1.0E-8, 1.0E-6, and 1.0E-4 M) and incubated for 2 hrs before being filtered with a filter membrane (0.22 μm). In all, 30 μl of sterile filtrate from each induced sample containing soluble S5 was spotted onto trypticase soy agar (TSA) plate in triplicates. Upon drying of spots, 0.1 ml of ln 7 at $OD_{600}$ of 0.2 in soft agar (1% peptone, 0.5% agar) pre-warmed at 55° C. was thinly filmed over the spotted TSA and allowed to dry completely. Resultant TSA plate was then incubated for 6 hrs at 37° C. before image analysis with Bio-Rad ChemiDoc XRS. To evaluate the effectiveness of the engineered system coupled with the sensing function, overnight culture of P. aeruginosa ln 7 was also harvested at $OD_{600}$ of 1.0 after redilution. The culture was filtered with a filter membrane (0.22 μm) and the sterile filtrate obtained, containing planktonic $3OC_{12}HSL$ was used to induce pTetR-LasR-pLuxR-S5-pLuxR-E7 (Top10). These procedures were repeated to capture inhibitory images for the engineered system that was activated by $3OC_{12}HSL$ natively produced from P. aeruginosa.

Co-Culturing of the Engineered E. coli and P. aeruginosa

GFP reporter plasmid pMRP9-1 and chloramphenicol-resistant plasmid pAWG1.1 were transformed into P. aeruginosa ln 7 and PAO1 using a method described hereinabove. Overnight cultures of P. aeruginosa (ln 7/PAO1 with pMRP9-1), pTetR-LasR-pLuxR-S5 (Top10), pTetR-LasR-pLuxR-E7 (Top10), and pTetR-LasR-pLuxR-S5-pLuxR-E7 (Top10) were diluted and harvested at an $OD_{600}$ of 1.0. pTetR-LasR-pLuxR-S5-pLuxR-E7 (Top10) was added to ln 7 or PAO1 in the ratio 4:1 to obtain a mixed culture with an overall cell density of 1.0E8 cfu/ml in 25 ml of MHB. The resultant mixture was grown for 15 hrs in a shaking flask culture set at 37° C. and 170 rpm. For fluorescence assays, the mixed culture was transferred into a transparent, flat-bottom 96-well plate in aliquots of 200 μl and assayed for background subtracted green fluorescence in a microplate reader (Biotek) at regular intervals of 3 hrs. The same procedures were repeated for pTetR-LasR-pLuxR-S5 (Top10) and pTetR-LasR-pLuxR-E7 (Top10) as negative controls. For cell viability assays, aliquots of P. aeruginosa in the mixed culture were quantified by CFU count on chloromphenicol selective agar plates at regular intervals of 5 hrs. The same procedures were repeated for pTetRLasR-pLuxR-S5 (Top10) and pTetR-LasR-pLuxR-E7 (Top10) as negative controls.

Percentage survival of planktonic P. aeruginosa was determined as follows in Equation (2):

$$\text{Percentage cell survival} = \frac{CFU \text{ of } P. \text{ aeruginosa in treated sample at time } t \times 100}{CFU \text{ of } P. \text{ aeruginosa treated with } WT \text{ } E. \text{ coli at time } t} \quad (2)$$

Live and Dead Fluorescent Microscopy

Overnight cultures of ln 7 and pTetR-LasR-pLuxR-S5-pLuxR-E7 (Top10) were diluted in LB and harvested at an $OD_{600}$ of 0.5 and 1.0, respectively. $3OC_{12}HSL$ from ln 7 was obtained after passing ln 7 culture through a filter membrane (0.22 μm) and the sterile filtrate was used to induce expression of engineered system by mixing it with pTetR-LasR-pLuxR-S5-pLuxR-E7 (Top10) in 1:1 mixing ratio to a total volume of 2 ml. The resultant culture was grown for 3 hrs and filtered with a similar membrane to obtain sterile S5 filtrate. The filtrate was mixed with ln 7 at $OD_{600}$ of 1.0 in 1:1 mixing ratio to a total volume of 2 ml and incubated for 3 hrs. One microliter of the final culture was stained with bacterial viability kit (Invitrogen) according to the manufacturer's instruction and analyzed with a fluorescent microscope (Zeiss Axio Scope A1).

Biofilm Inhibition Assay

P. aeruginosa (ln 7/PAO1 with pAWG1-1) conferred with chloramphenicol resistance was mixed with pTetR-LasR-pLuxR-S5-pLuxR-E7 (Top10) in the ratio 1:4 to obtain a mixed culture with an overall cell density of 1.0E8 cfu/ml in 6 ml of MHB. The resultant mixture was transferred to the wells of a polystyrene microtiter plate (Iwaki) in aliquots of 1 ml each and grown at 37° C. and 150 rpm. After 18 hrs of growth, biofilm on the microtiter plate was rinsed and recovered in fresh MHB by sonication and quantified by CFU count on chloramphenicol-selective plate (100 mg/ml). The same procedures were repeated for ln 7 treated with pTetR-LasR-pLuxR-S5 (Top10) and pTetR-LasR-pLuxR-E7 (Top10), and PAO1 treated with pTetR-LasR-pLuxR-S5-pLuxR-E7 as negative controls. Percentage survival of P. aeruginosa biofilm was determined as follows in Equation (3):

$$\text{Percentage biofilm survival} = \frac{CFU \text{ of } P. \text{ aeruginosa biofilm in treated sample} \times 100}{CFU \text{ of } P. \text{ aeruginosa biofilm in treated with } WT \text{ } E. \text{ coli}} \quad (3)$$

Confocal Microscopy of Biofilm

Mixed bacteria cultures of P. aeruginosa (ln 7 with pMRP9-1) and engineered E. coli systems were grown in MHB in 50 ml tubes containing sterile glass slide. Biofilm developed on the glass slides after 18 hrs of growth was rinsed in PBS, dried, and visualized by confocal laser scanning microscopy (Zeiss LSM 510). Collected Z-stack biofilm images were reconstructed using Zeiss 2.5D software.

Examples

Characterization of the Sensing Device

Figure 2A:
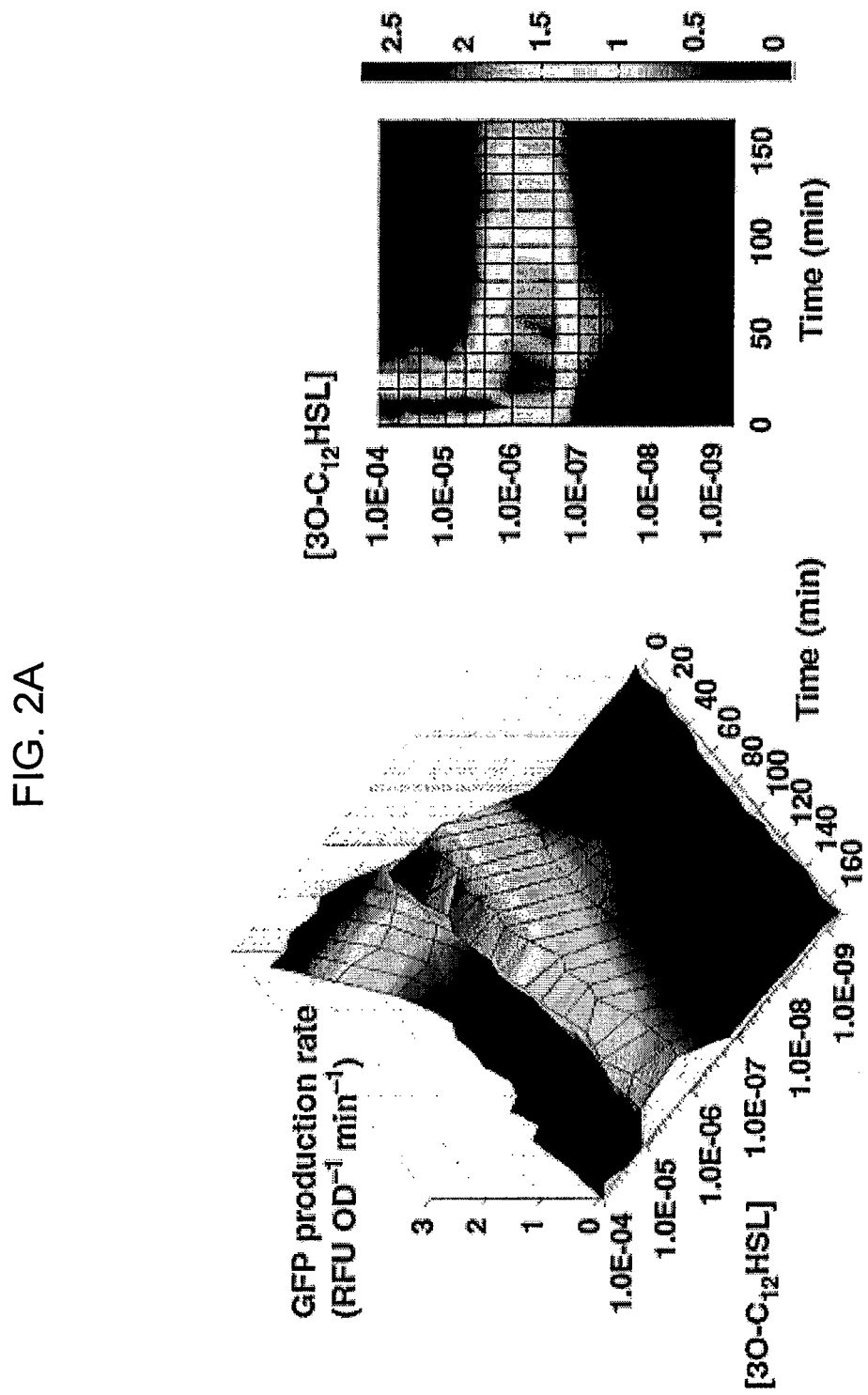
FIG. 2A shows GFP production rate per cell over time at different $3OC_{12}HSL$ inducer concentrations.
Figure 7B:
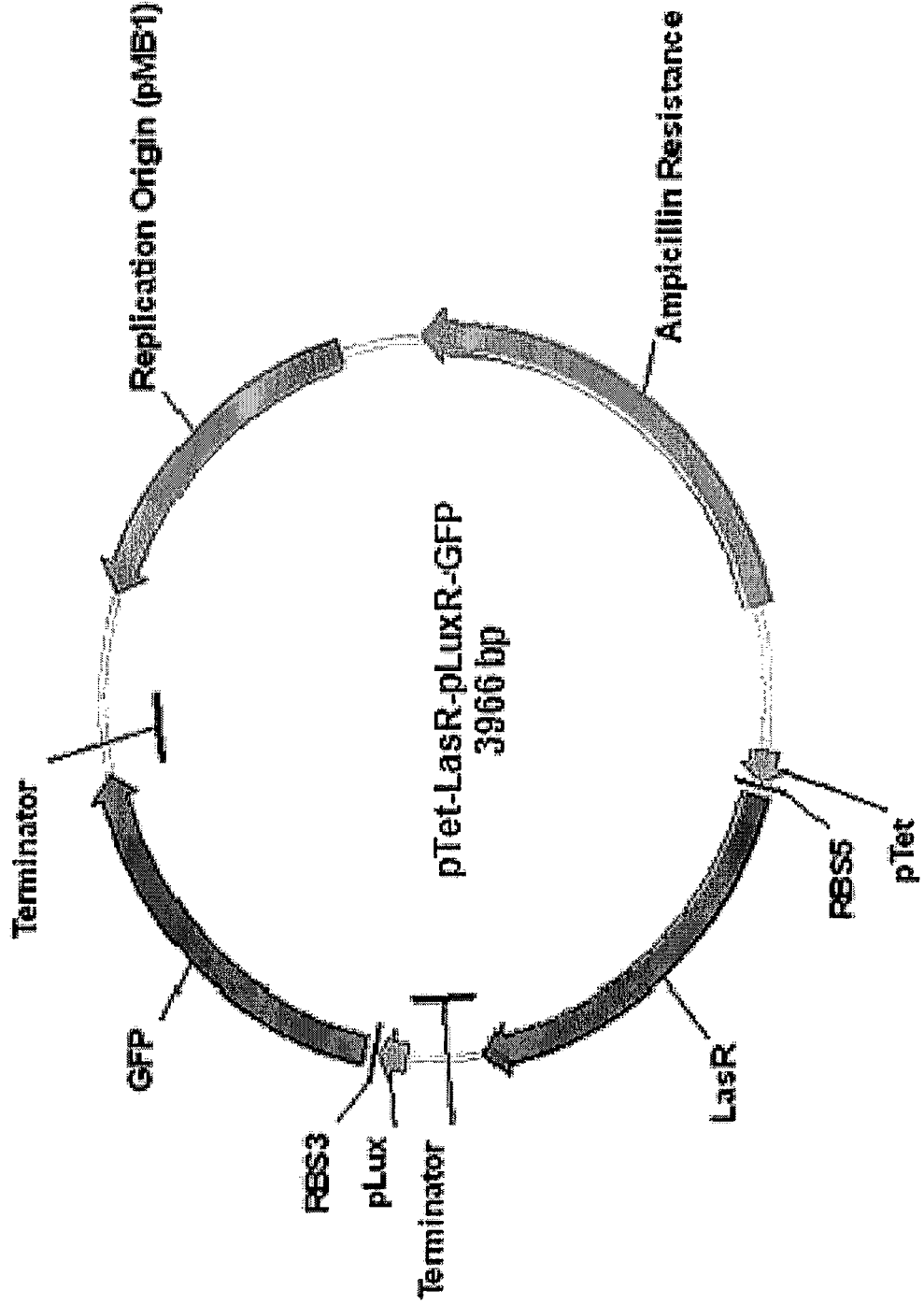
FIG. 7B shows a sensing device coupled to GFP, pTetR-LasR-pLuxR-GFP. This construct was used as a measurement tool for characterization of the sensor (pTetR-LasR-pLuxR).

To evaluate and characterize the sensing device, the gene encoding the green fluorescent protein (GFP) was fused to the sensing device (i.e., pTetR-LasR-pLuxR-GFP; the plasmid map is shown in FIG. 7B) and the GFP expression was monitored at a range of concentrations of $3OC_{12}HSL$. From the measured GFP synthesis rates (FIG. 2A), a basal expression level of 0.216 RFU per OD per minute without induction, followed by a sharp increase in GFP production rate as the concentration of $3OC_{12}HSL$ was increased beyond 1.0E-7 M was observed. This transition peaked at 1.0E-6 M of $3OC_{12}HSL$ and exhibited a sharp decline afterward. The optimal detection range of the sensing device was between 1.0E-7 and 1.0E-6 M $3OC_{12}HSL$. As a comparison, it has been estimated in the art extracellular concentration of $3OC_{12}HSL$ to be in the range of 1.0E-6 to 1.0E-4 M within proximity to the site of P. aeruginosa infection.

Transfer Function of the Sensing Device

Figure 2B:
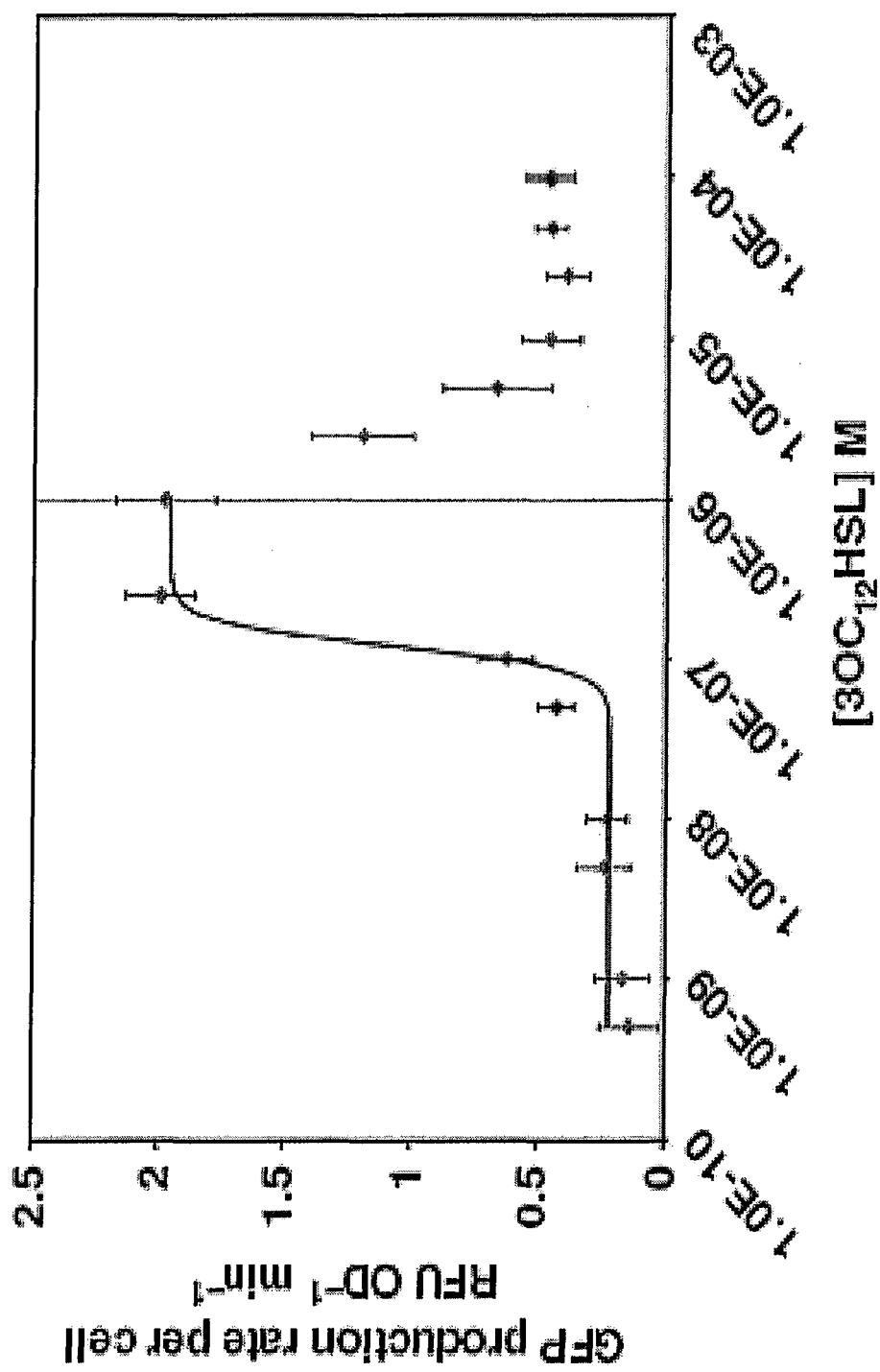
FIG. 2B shows time-averaged GFP production rate per cell at different input $3OC_{12}HSL$ concentrations, showing that the optimal operating concentrations for the sensing device range from 1.0E-7 to 1.0E-6 M $3OC_{12}HSL$. Error bar represents the standard deviation of statistical means between 20 and 80 mins after induction, performed with six replicates.

One important characteristic of the sensing device was the transfer function that describes the static relationship between the input ($3OC_{12}HSL$) and output (GFP production rate) of the sensing device. The transfer function was determined by fitting an empirical mathematical model (Hill equation) to the experimental data where the input $3OC_{12}HSL$ concentration is <1.0E-6 M. The best fit model demonstrated that the static performance of the sensing device follows a Hill equation below the input concentration of 1.0E-6 M $3OC_{12}HSL$ (FIG. 2B). The model showed that the sensing device saturated at a maximum output of 1.96 RFU per OD per minute at input concentration >3.3E-7 M but <1.0E-6 M $3OC_{12}HSL$, and the switch point for the sensing device was 1.2E-7 M $3OC_{12}HSL$, the input concentration at which output is at half-maximal. Since this switch point concentration is smaller than the concentration of $3OC_{12}HSL$ present (1.0E-6 to 1.0E-4 M) within proximity to the site of *P. aeruginosa* infection, the sensing device would be sensitive enough to detect the amount of $3OC_{12}HSL$ natively produced by *P. aeruginosa*.

Detection of the Native Autoinducer Produced by *P. aeruginosa*

The characterization of the sensing device as described herein above indicated that it produced an optimal output at 1.0E-7 to 1.0E-6 M $3OC_{12}HSL$. To verify that the sensing device would be able to sense the amount of $3OC_{12}HSL$ natively produced by *P. aeruginosa*, the sensing device coupled with a GFP reporter (i.e., pTetR-LasR-pLuxR-GFP) was induced using the filtered culture of *P. aeruginosa* ln 7, a clinical isolate that is sensitive to pyocin S5. Measurements show that GFP synthesis rate for the isolate ln 7 was 1.375 RFU per OD per minute. This value was above the minimum synthesis rate and greater than the half-maximal of the sensing device. This confirmed that the sensing device was able to detect the natively produced $3OC_{12}HSL$. Further, the GFP synthesis rate measured and the model (Equation (1)) was used to gain an insight into the amount of $3OC_{12}HSL$ natively produced by the isolate. The average concentration of $3OC_{12}HSL$ in the liquid culture of the *P. aeruginosa* strain was estimated to be ~1.0E-6 M $3OC_{12}HSL$. This measurement was coherent with the extracellular concentration of $3OC_{12}HSL$ estimated in the art which is between 1.0E-6 and 1.0E-4 M.

Characterization of the Lysing Device

Figure 3A:
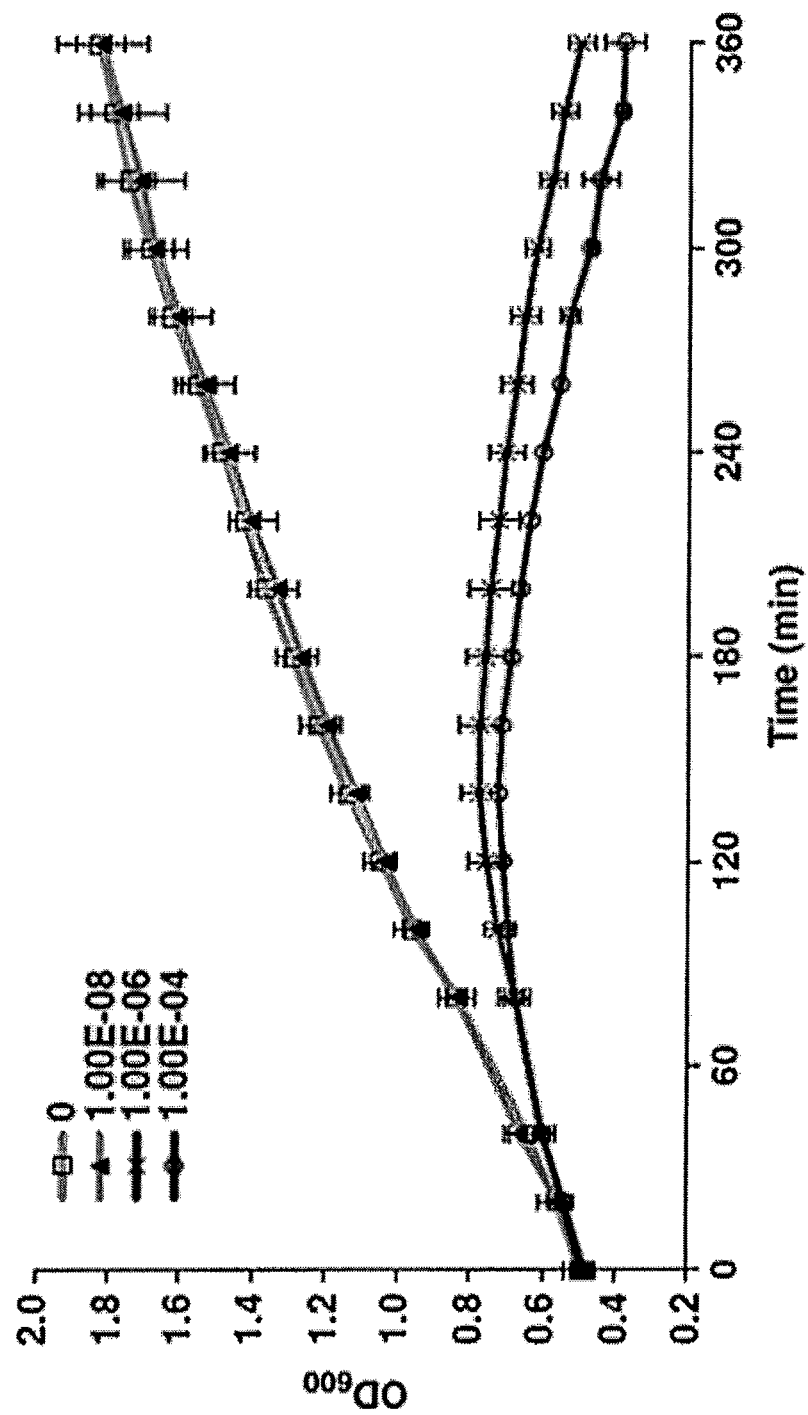
FIG. 3A shows the growth curve of *E. coli* expressing E7 lysis protein after induction with different concentrations of $3OC_{12}HSL$.
Figure 3B:
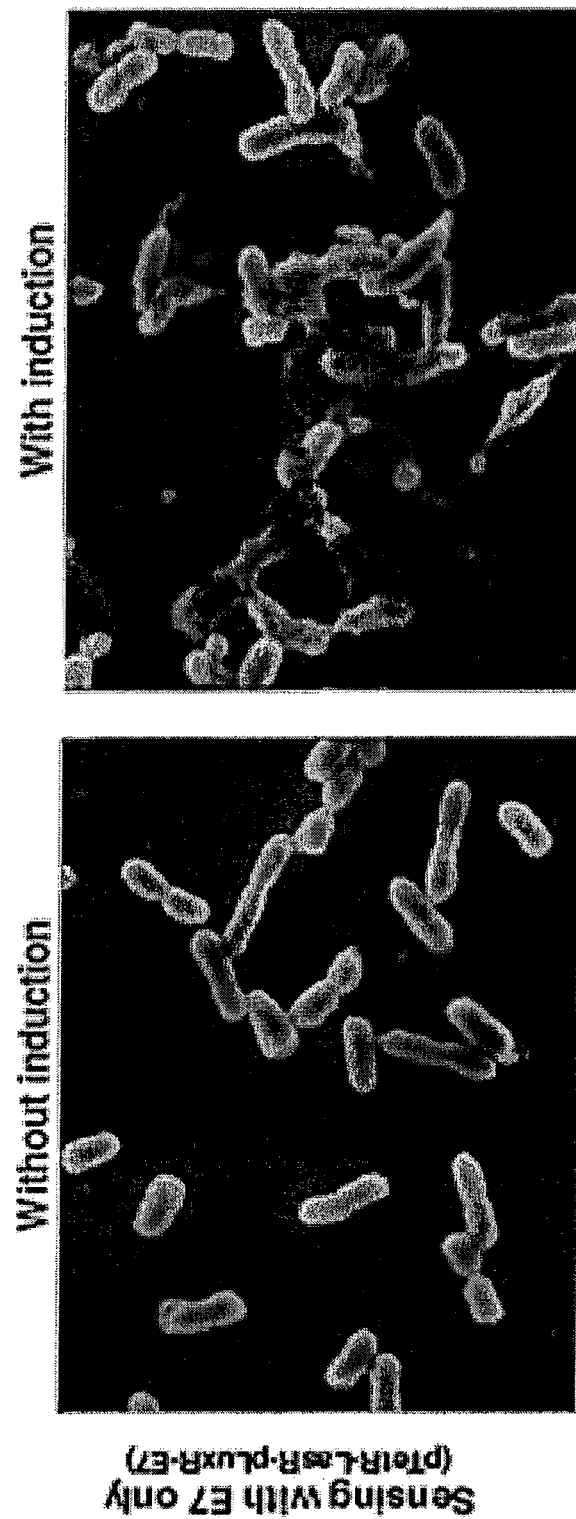
FIG. 3B and FIG. 3C show the effects of lysis protein on *E. coli* surface morphology as observed using a Field Emission Scanning Electron Microscope (FESEM). It was observed that the surface of the *E. coli* was damaged when *E. coli* carrying pTetR-LasR-pLuxR-E7 and *E. coli* carrying pTetR-LasR-pLuxR-S5-pLuxR-E7 (the final system) were induced with $3OC_{12}HSL$. Scale bar: 1 mm. Error bar represents the standard deviation of four replicates.
Figure 7C:
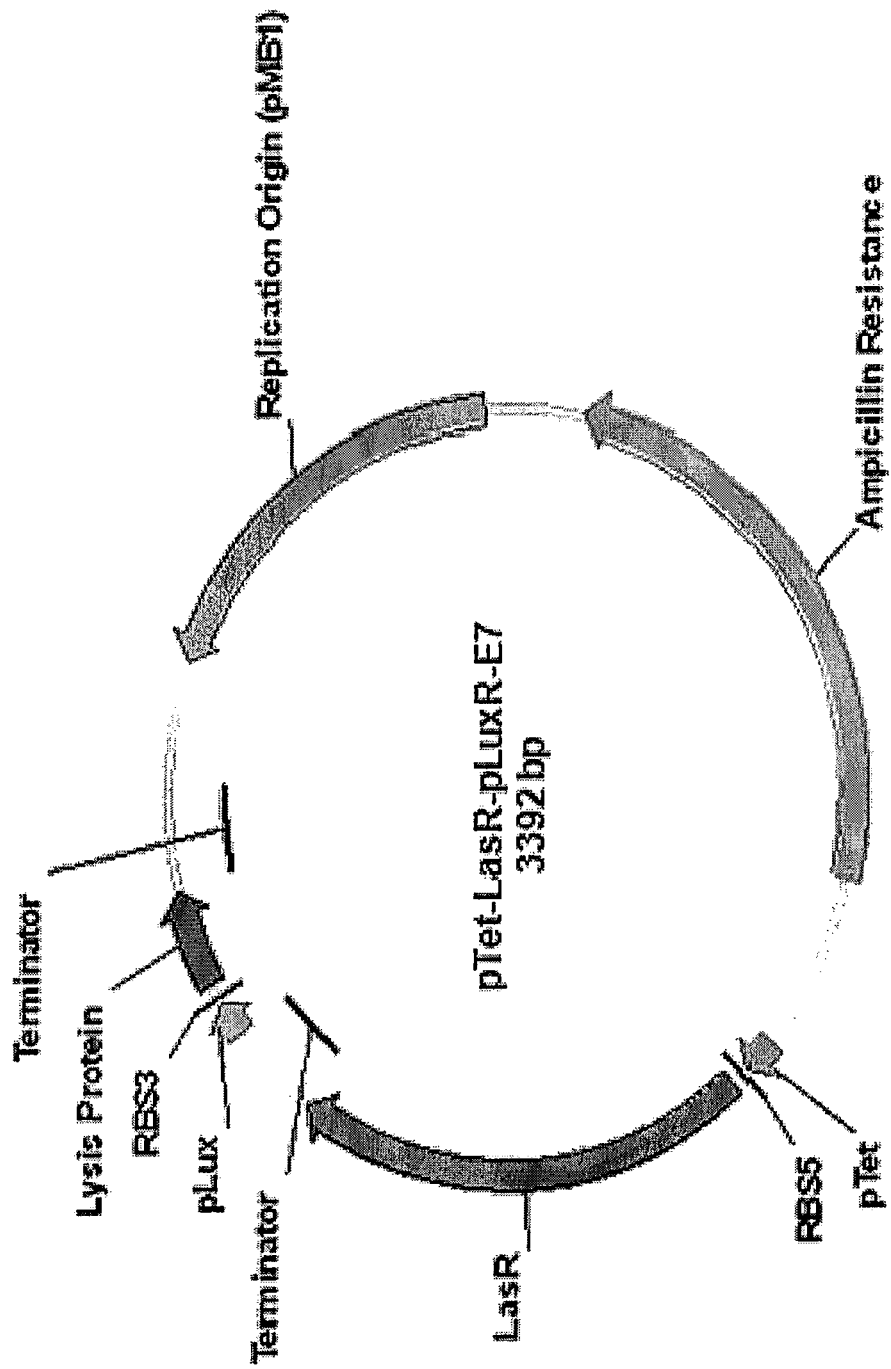
FIG. 7C shows a sensing device with E7 lysis, pTetR-LasR-pLuxR-E7. This construct was used for the characterization of E7 lysis protein whose function is to disrupt cell membrane for the release of pyocin.

The system according to various embodiments was designed to release pyocin S5 through lysis upon detection of *P. aeruginosa*. To determine the lysis activity of the system, the behavior of the E7 lysis protein under the transcriptional control of the sensing device before integrating both the pyocin S5 and E7 genes into the system was characterized. The E7 lysis gene was ligated downstream to the sensing device (i.e., pTetR-LasR-pLuxR-E7; the plasmid map is shown in FIG. 7C) and its performance was evaluated in the *E. coli* chassis over time by measuring absorbance at $OD_{600}$ at a range of concentrations of $3OC_{12}HSL$. FIG. 3A shows that at 0 and 1.0E-8 M $3OC_{12}HSL$, the growth rates of *E. coli* underwent no noticeable transition into a lysis state. However, at higher concentrations of $3OC_{12}HSL$ (i.e., 1.0E-6 and 1.0E-4 M), the cells exhibited a significant reduction in optical density, likely due to the lysis activity. In this example, it is implied that 1.0E-6 M or higher concentrations of $3OC_{12}HSL$ cause observable cell lysis with a delay of ~120 mins. To verify the effect of the lysis, cell integrity was examined with and without 1.0E-6 M $3OC_{12}HSL$ using field emission scanning electron microscopy (FESEM). FIG. 3B shows that *E. coli* containing pTetR-LasR-pLuxR-E7 and induced with $3OC_{12}HSL$ appeared shriveled with corrugated surface morphology, in contrast to the distinct 'rod-like' features of the cells that were not induced with $3OC_{12}HSL$. To further confirm that the lysis activity may be sustained in the final system including pyocin S5, the morphology of *E. coli* containing the final system (i.e., pTetR-LasR-pLuxR-S5-pLuxR-E7; FIG. 1) was monitored using FESEM.

Figure 3C:
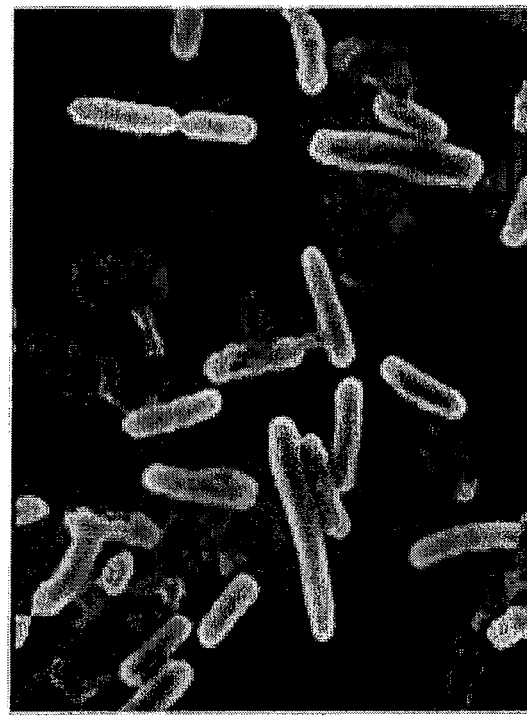
Figure 3C:
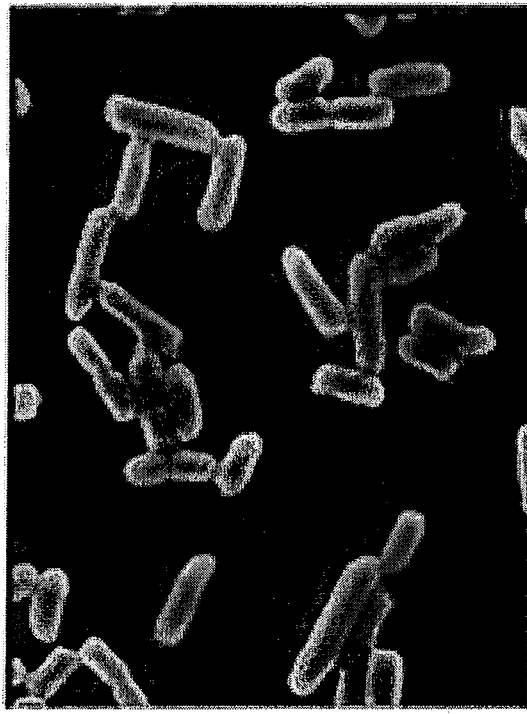

FIG. 3C shows that *E. coli* cells having the final system and induced with $3OC_{12}HSL$ also appeared shriveled with corrugated surface morphology, whereas *E. coli* cells having the final system but not induced with $3OC_{12}HSL$ remained 'rod-like' in shape. These observations were similar to that obtained in earlier examples with *E. coli* containing pTetR-LasR-pLuxR-E7. This suggests that $3OC_{12}HSL$ induced the lysis of the *E. coli* containing the final system.

Figure 4A:
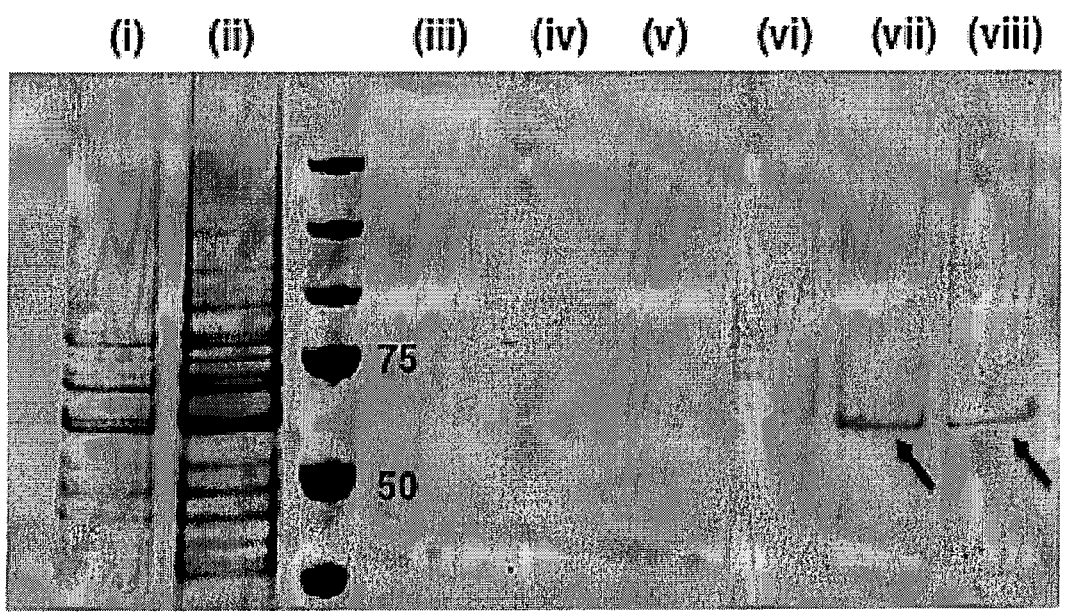
FIG. 4A shows sodium dodecyl sulfate polyacrylamide gel electrophoresis (SDS-PAGE) of (i, ii) total extracellular proteins and (iii-viii) IMAC purified His-tagged S5 protein sampled from the extracellular supernatant. Total extracellular proteins exported from (i) *E. coli* carrying pTetR-LasR-pLuxR-S5 (without lysis device) was significantly lesser than that exported from (ii) *E. coli* carrying pTetR-LasR-pLuxR-S5-pLuxR-E7 (the final system) as indicated in darker lanes of (ii) relative to (i). (iii-v): *E. coli* carrying pTetR-LasR-pLuxR-S5 (without lysis device) at 0, 2, and 4 hrs after induction. (vi-viii) *E. coli* carrying pTetR-LasR-pLuxR-S5-pLuxR-E7 (the final system) at 0, 2, and 4 hrs after induction. It can be seen that pyocin S5 (57 kDa; arrowed) was only detectable in lanes that corresponded to *E. coli* carrying the final system and not in lanes of *E. coli* without the lysis device. Ladder used was Bio-Rad's Precision Plus Protein standards.
Figure 4B:
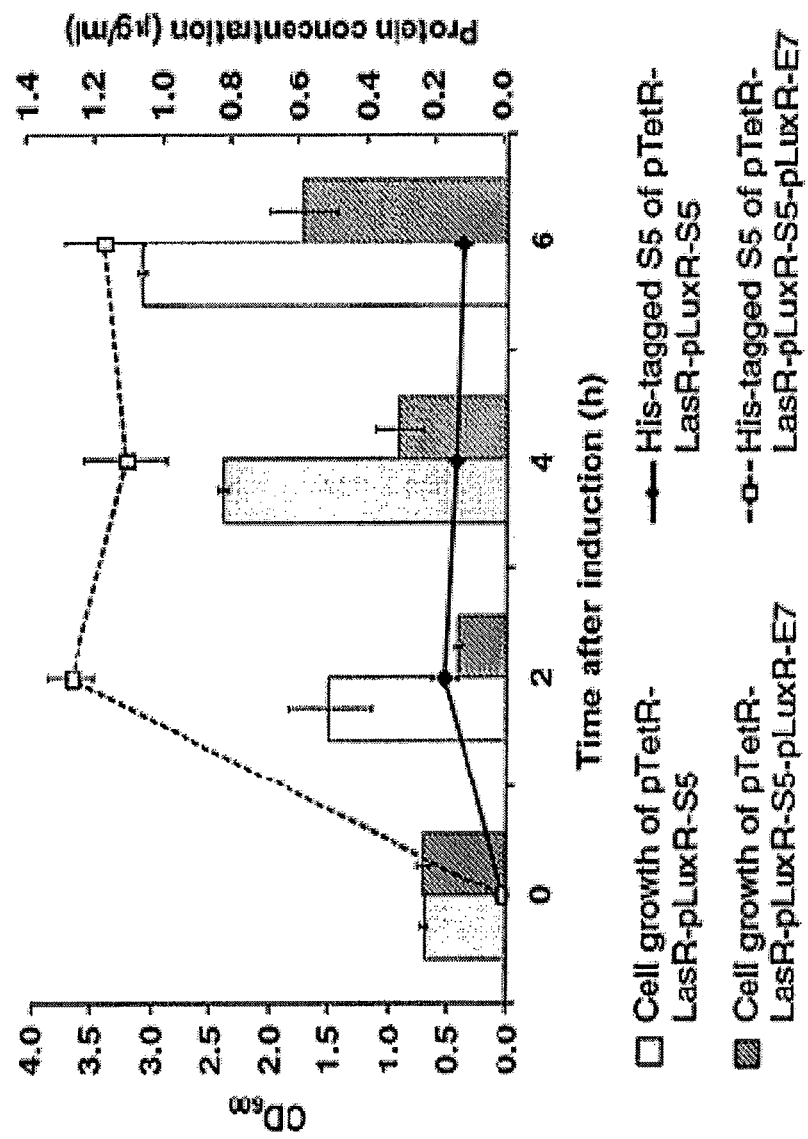
FIG. 4B shows the characterization of lysis device in the final system by optical density (bar graphs) and concentration of pyocin released (lines) after induction. An impulse release of pyocin S5 was observed at 2 hrs after induction, followed by a sustained steady-state release in the final system (dotted lines). Optical density of the final system was characterized by an initial decrease at 2 hrs after induction, indicative of the onset of lysis, after which the regrowth of engineered *E. coli* occurs (shaded bar). Correspondingly, the concentration of pyocin released in *E. coli* without the lysis device (solid line) was ⅛ that of the final system with a continually increasing optical density (unshaded bar). Error bar represents the standard deviation of two replicates.

In line with the overall objective of the E7 lysis device in mediating the export of pyocin, the efficiency of the lysis device in the final system by measuring the amount of the released protein was studied. After induction with 1.0E-6 M $3OC_{12}HSL$, histidine-tagged S5 protein was purified by immobilized metal affinity chromatography from the filtered supernatant and analyzed by SDS-PAGE and Bradford assay. FIG. 4A shows that distinct bands that corresponded to pyocin S5 were observed on the SDS-PAGE of the final system (i.e., pTetRLasR-pLuxR-S5-pLuxR-E7), while no bands were seen in lanes without the lysis device (i.e., pTetR-LasR-pLuxR-S5; the plasmid map is shown in FIG. 7D). The observations were validated by estimating the protein concentrations in the supernatant with Bradford assay and showed that the amount of pyocin released by the final system was eight times higher than the system without the lysis device (FIG. 4B). The dynamic performance of the lysis device in the final system was characterized by an impulse release of protein 2 hrs after induction, followed by a steady-state response.

Verification of the Final System with the Sensing, Killing, and Lysing Devices

The engineered microbes according to various embodiments are able to sense natively produced AHL $3OC_{12}HSL$, which subsequently triggers cell lysis. To further determine whether the sensing of $3OC_{12}HSL$ also leads to the killing of *P. aeruginosa* designed, the growth of *P. aeruginosa* was monitored in the presence of the engineered *E. coli* containing the final system.

Figure 8A:
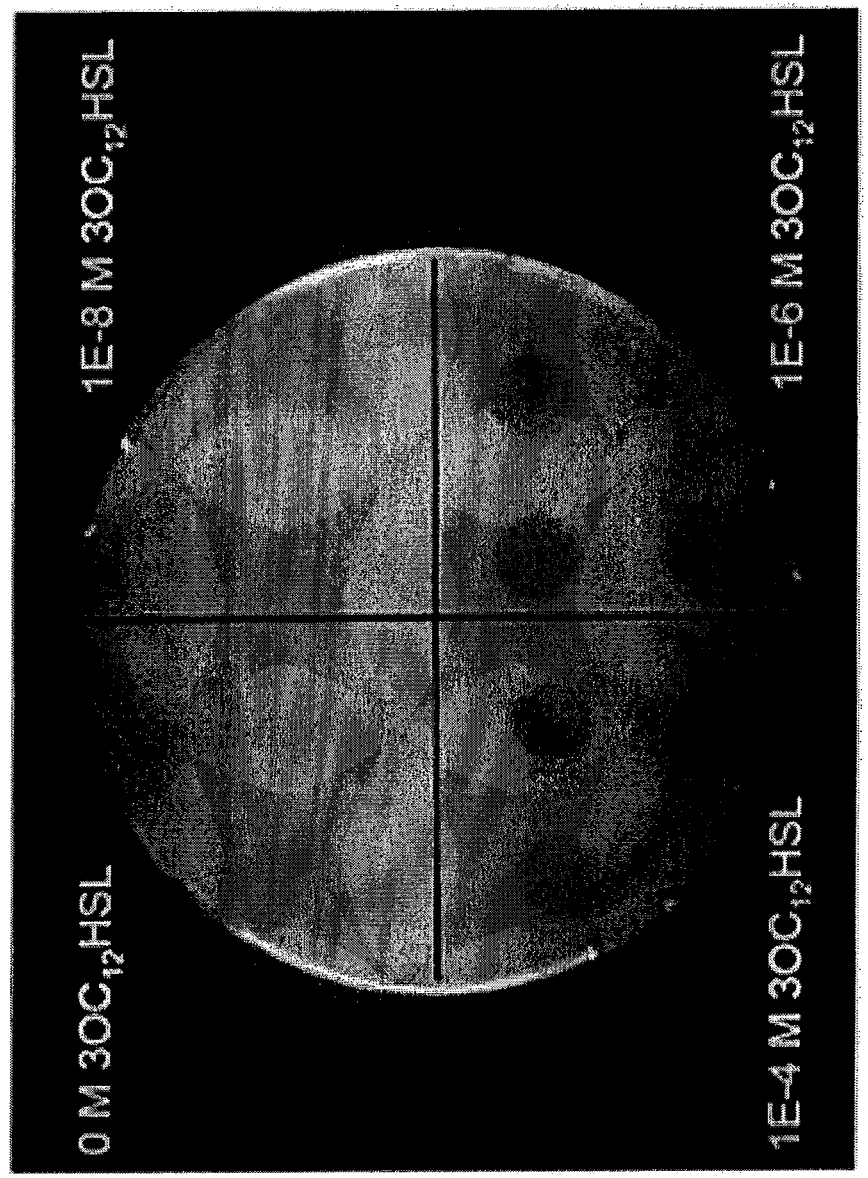
FIG. 8A shows agar overlay assay of *P. aeruginosa* after exposure to supernatant of the *E. coli* carrying pTetR-LasR-pLuxR-S5-pLuxR-E7 (the final system) at different $3OC_{12}HSL$ concentrations. Faint inhibition areas were observed with 0 M and 1.0E-8 M $3OC_{12}HSL$. It is shown that supernatant of engineered *E. coli* culture induced by 1.0E-6 M $3OC_{12}HSL$ produced wider and clearer inhibition zones relative to other inducer concentrations.

First, to determine the concentration of $3OC_{12}HSL$ that causes a significant growth inhibition and confirm that the concentration falls within the range of concentrations of $3OC_{12}HSL$ naturally produced by *P. aeruginosa*, the engineered *E. coli* was exposed to commercial $3OC_{12}HSL$ at 0, 1.0E-8, 1.0E-6, and 1.0E-4 M, and the filtered supernatants were added onto *P. aeruginosa*-grown agars. The growth of *P. aeruginosa* was clearly inhibited by the filtered supernatants of the *E. coli* cultures exposed to 1.0E-6 and 1.0E-4 M $3OC_{12}HSL$, whereas very faint inhibition zones were observed at 0 and 1.0E-8 M, likely due to the basal expression of pyocin S5 and E7 (FIG. 8A).

Figure 8B:
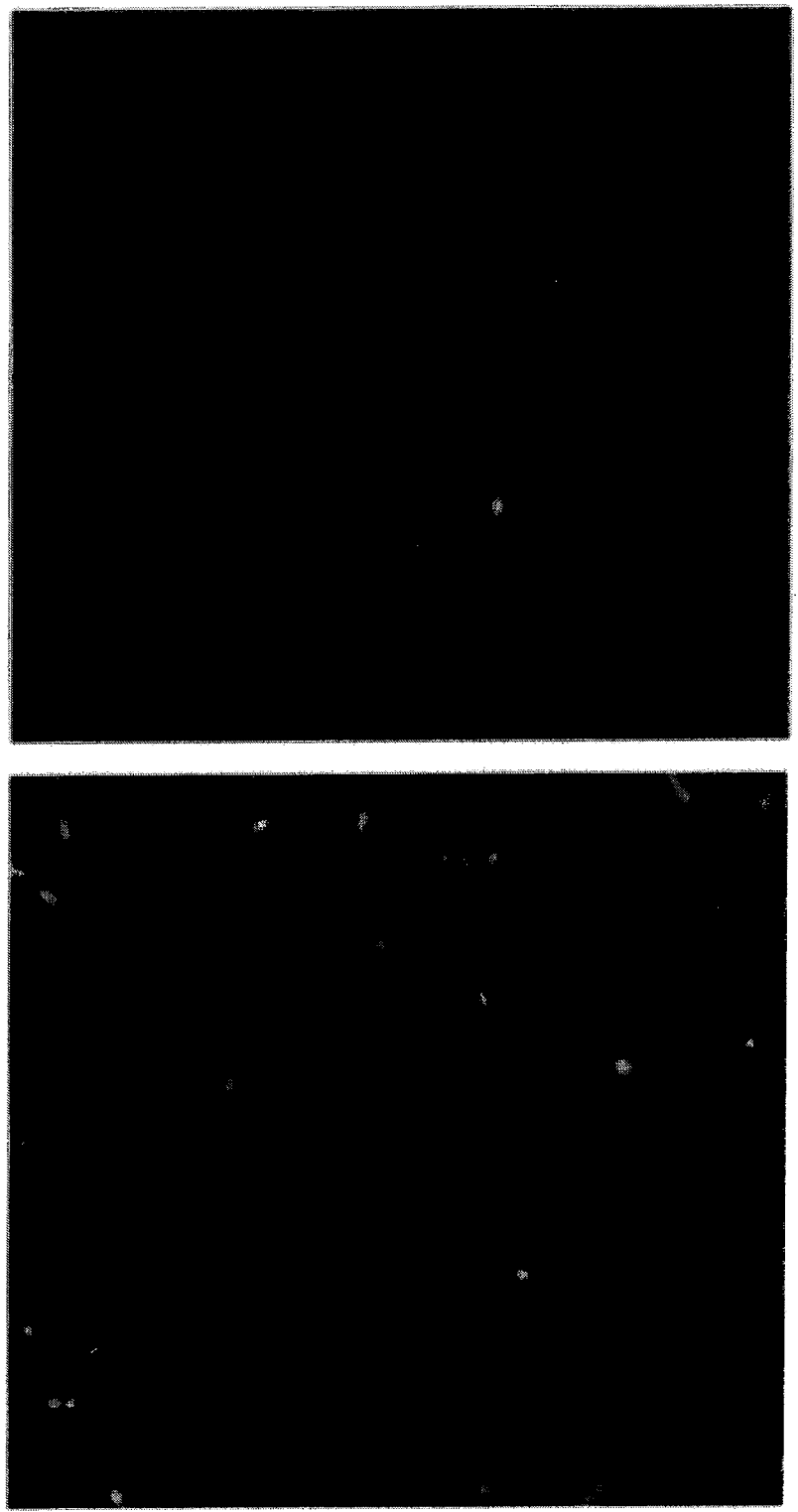
FIG. 8B shows *P. aeruginosa* cells stained using the LIVE/DEAD cell viability assay. It is shows that more PI-stained *P. aeruginosa* cells were present when *P. aeruginosa* was exposed to supernatant of the *E. coli* carrying the final system that was induced by $3OC_{12}HSL$, whereas all *P. aeruginosa* cells exposed to supernatant of wild-type *E. coli* (control) were stained with SYTO 9 (green). Scale bar: 5 μm.

Second, to further confirm the inhibition effects, *P. aeruginosa* was examined upon exposure to the supernatant of the *E. coli* cultures with 1.0E-6 M $3OC_{12}HSL$ using the LIVE/DEAD cell viability assay. As seen under microscope, many *P. aeruginosa* cells exposed to the supernatant of the engineered *E. coli* were stained with the PI dye, which stains a dead cell, whereas those that were incubated with the wild-type *E. coli* were mostly stained with the SYTO 9 dye, which stains a live cell (FIG. 8B). This suggests that the engineered *E. coli* in accordance to various embodiments carrying the final system can kill *P. aeruginosa* in response to as low as 1.0E-6 M $3OC_{12}HSL$. Since earlier estimation indicated that the concentration of $3OC_{12}HSL$ natively produced by *P. aeruginosa* was ~1.0E-6 M, this outcome may imply that this killing activity would be sustained against *P. aeruginosa* in response to its producing $3OC_{12}HSL$.

Figure 5A:
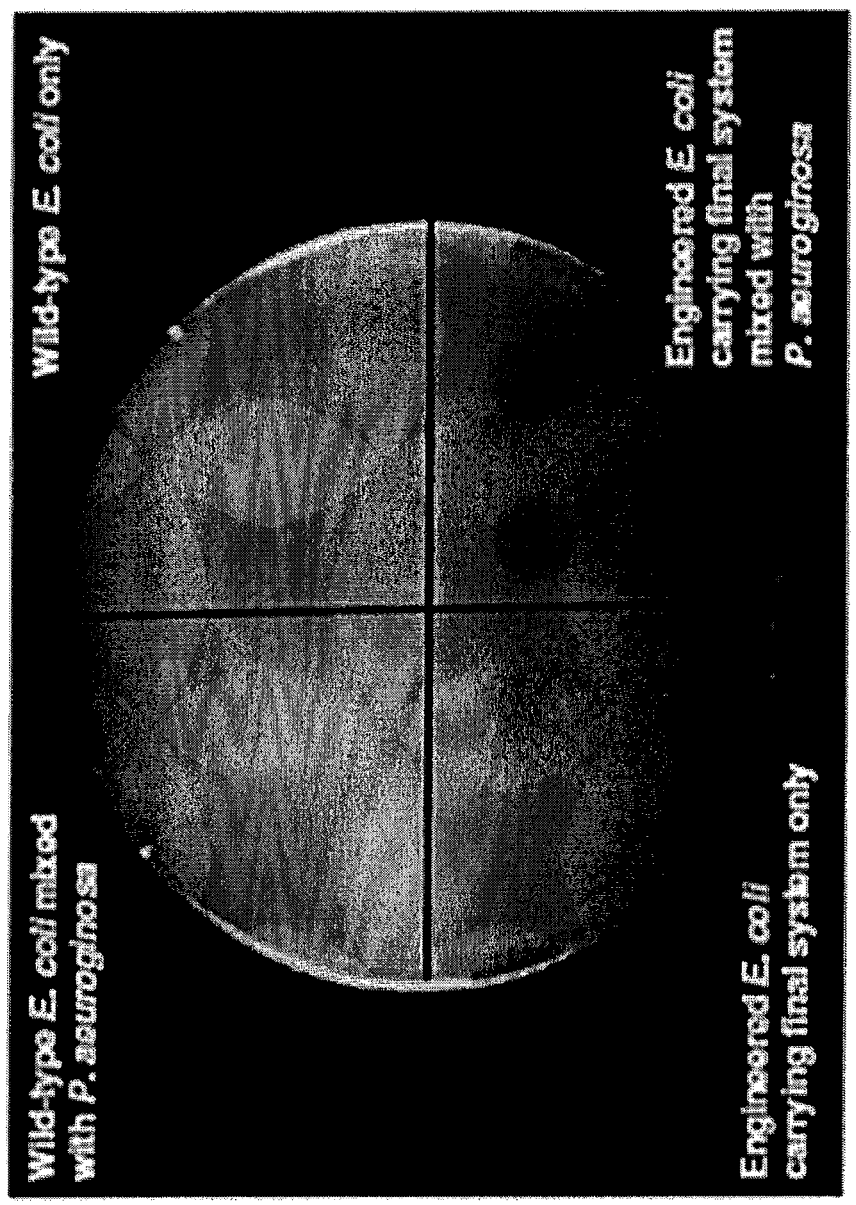
FIG. 5A shows agar overlay assay of *P. aeruginosa* after exposure to supernatant of four different cultures. First, *P. aeruginosa* exposed to supernatant of wild-type *E. coli* showed no bactericidal activity. Second, *P. aeruginosa* exposed to supernatant of wild-type *E. coli* mixed with *P. aeruginosa* produced no inhibition zones. Third, exposure to supernatant of *E. coli* carrying pTetR-LasR-pLuxRS5-pLuxR-E7 (final system) did not produce any inhibition as well. Fourth, only *P. aeruginosa* exposed to supernatant of *E. coli* carrying final system with *P. aeruginosa* displayed clear inhibition zones, which suggested that the system produced sufficient pyocin S5 to exhibit bactericidal activity.

Therefore, subsequently, to confirm the killing activity by the native $3OC_{12}HSL$ produced by *P. aeruginosa*, the filtered supernatant of *P. aeruginosa* cultures was mixed with the *E.* coli cultures, whose supernatant was then added to *P. aeruginosa*-grown agars. FIG. 5A shows that *P. aeruginosa* growth was significantly inhibited by the engineered *E. coli* cultures exposed to the supernatant of *P. aeruginosa* cultures, while neither with the wild-type *E. coli* cells nor without the *P. aeruginosa* supernatant led to growth inhibition. This indicates that the final system produces pyocin S5 and E7 in response to the $3OC_{12}HSL$ natively produced by *P. aeruginosa*, which resulted in the killing of *P. aeruginosa*.

Figure 5B:
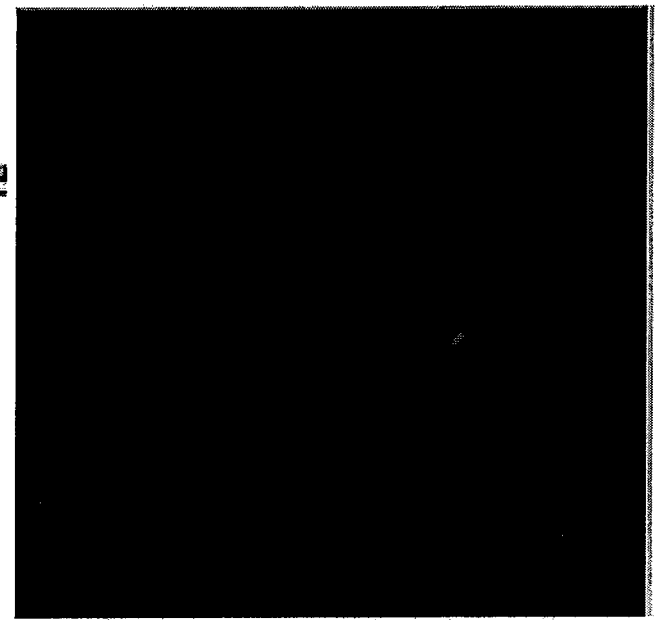
FIG. 5B shows *P. aeruginosa* cells stained using the LIVE/DEAD cell viability assay. Many *P. aeruginosa* cells were stained with PI dye, which indicate dead cells, when exposed to supernatant of engineered *E. coli* carrying the final system that was induced by native $3OC_{12}HSL$ produced by *P. aeruginosa*.
Figure 5B:
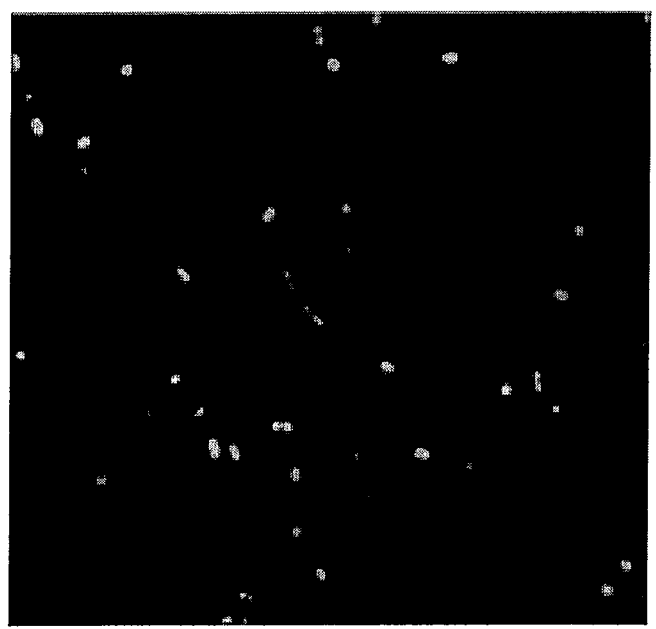

To further visualize the inhibition effects on *P. aeruginosa* by the engineered *E. coli* in accordance to various embodiments, *P. aeruginosa* cells were stained using the LIVE/DEAD cell viability assay. FIG. 5B shows that many *P. aeruginosa* cells exposed to the supernatant of the engineered *E. coli* induced with native $3OC_{12}HSL$ were stained with the PI dye, whereas the cells incubated with the wild-type *E. coli* were mostly stained with the SYTO 9 dye (green). This suggests that the engineered *E. coli* in accordance to various embodiments carrying the final system can kill *P. aeruginosa* in the presence of native $3OC_{12}HSL$ produced by *P. aeruginosa*.

To verify that the engineered *E. coli* that contains the final system in accordance to various embodiments (e.g., pTetR-LasR-pLuxR-S5-pLuxR-E7) exerts a killing activity against *P. aeruginosa* in a mixed culture, the growth of *P. aeruginosa* co-cultured with the engineered *E. coli* in the ratio 1:4 was monitored.

Figure 5C:
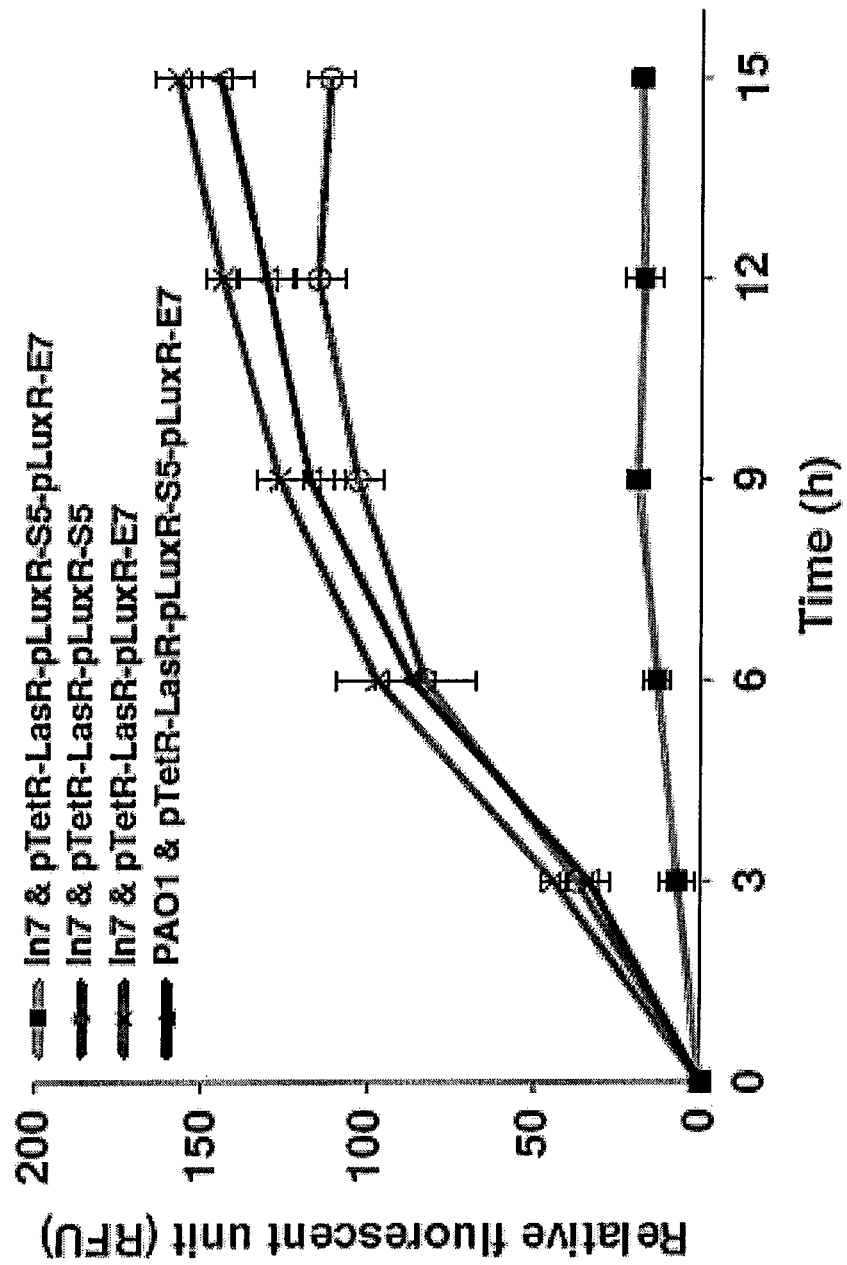
FIG. 5C shows fluorescence measurement of *P. aeruginosa* that constitutively expresses GFP in mixed culture with engineered *E. coli*. Analysis of the mixed culture with the engineered *E. coli* carrying pTetR-LasR-pLuxR-E7 and pTet-LasRpLuxR-S5 shows an exponential increase in the fluorescence readings, whereas the mixed culture with *E. coli* carrying pTetR-LasR-pLuxR-S5-pLuxR-E7 (the final system) exhibited no increase in the readings. This may suggest that the growth of *P. aeruginosa* was significantly inhibited in the mixed culture with engineered *E. coli* carrying the final system. PAO1, which pyocin S5 was derived from, was included as a negative control. Error bar represents the standard deviation of six replicates.

To determine the growth inhibition of *P. aeruginosa* in the mixed culture, *P. aeruginosa* that constitutively expresses GFP and *E. coli* that is without either the pyocin S5 or E7 lysis devices as negative controls was used. FIG. 5C shows that the GFP expression level of the *P. aeruginosa* co-cultured with the *E. coli* that carries the final system remained low and almost constant, whereas the GFP level underwent an exponentially increase when *P. aeruginosa* was cultured with the negative control *E. coli* systems.

To verify the efficiency in growth inhibition, CFU count on mixed cultures using *P. aeruginosa* that was transformed with chloramphenicol-resistant plasmid was performed. FIG. 5D shows that the engineered *E. coli* inhibited the growth of *P. aeruginosa* by >99% while continuous growths were apparent in *P. aeruginosa* co-cultured with incomplete *E. coli* systems missing either the pyocin S5 or E7 lysis devices.

Figure 8C:
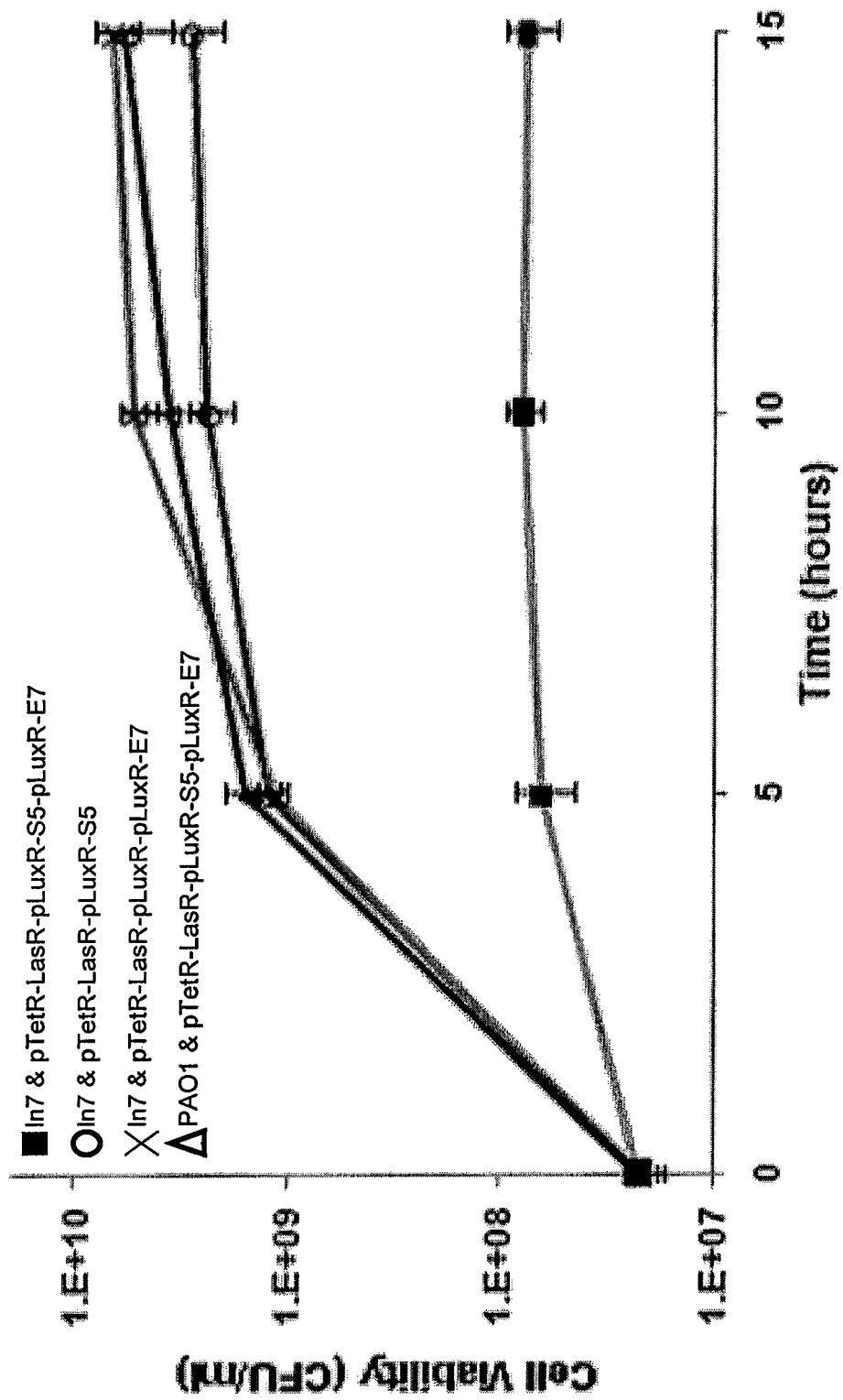
FIG. 8C shows CFU count of *P. aeruginosa* (carrying chloramphenicol-resistant plasmid pAWG1-1) in a mixed culture with engineered *E. coli*. To study whether the engineered *E. coli* carrying the final system can inhibit growth of *P. aeruginosa* in mixed culture, clinical isolate ln 7 and pyocin resistant control strain PAO1 was co-cultured with engineered *E. coli* in the ratio 1:4 and quantified by viable cell count of *Pseudomonas*. Additionally, ln 7 was also co-cultured with control *E. coli* missing either the pyocin S5 or E7 lysis devices. It is shown that only the final system (i.e. pTetR-LasR-pLuxR-S5-pLuxR-E7), complete with sensing, killing and lysis devices are capable of inhibiting the growth of *P. aeruginosa* for 15 hours. Error bar represents the standard deviation of 3 independent replicates.

The example also implies that the engineered system in accordance to various embodiments was activated only after the pathogen entered the late exponential and stationary phase when the autoinducers were released (FIG. 8C).

Figure 6A:
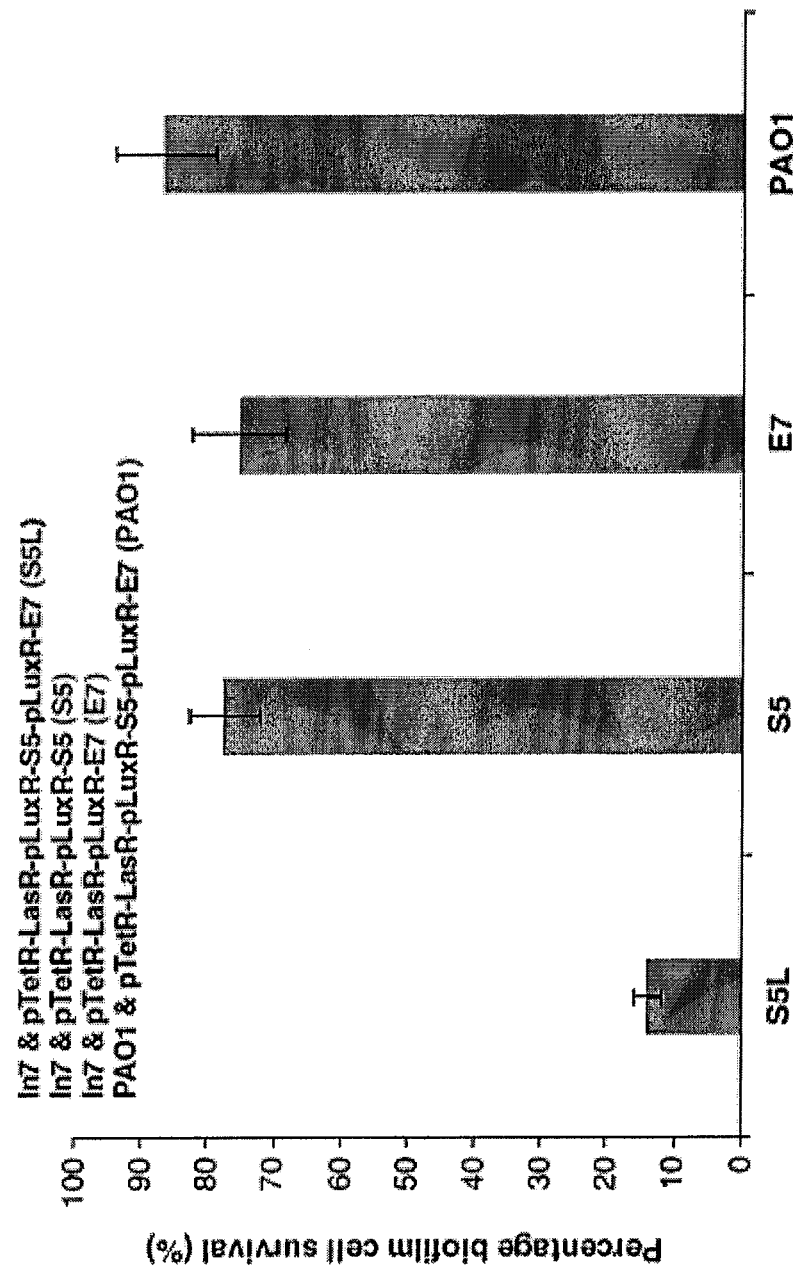
FIG. 6A shows the percentage survival of *P. aeruginosa* biofilm carrying chloramphenicol-resistant plasmid. *Pseudomonas* biofilm was grown in a polystyrene 24-well plate in the presence of the engineered *E. coli* for 18 hrs and quantified by viable cell count using chloramphenicol selection. The formation of *Pseudomonas* biofilm was inhibited by close to 90% with the engineered *E. coli* carrying the final system (pTetR-LasR-pLuxR-S5-pLuxRE7) as compared with biofilm grown with wild-type *E. coli* or incomplete *E. coli* system missing either pyocin S5 or E7 lysis genes. *P. aeruginosa* PAO1, which pyocin S5 was derived from, was included as a negative control. Error bar represents the standard deviation of six replicates.

To examine the potential application of the engineered system in accordance to various embodiments against a pseudo disease state of *Pseudomonas*, a static biofilm inhibition assay was performed by culturing *P. aeruginosa* carrying a chloramphenicol-resistance plasmid with the engineered *E. coli*. FIG. 6A shows that the engineered *E. coli* inhibited the formation of *P. aeruginosa* biofilm by close to 90%. This observation is in stark contrast to the pyocin-resistant control strain PAO1 and pyocin-sensitive clinical isolate ln 7 subjected to treatment with *E. coli* having the systems missing either the pyocin S5 or E7 lysis gene.

Figure 6B:
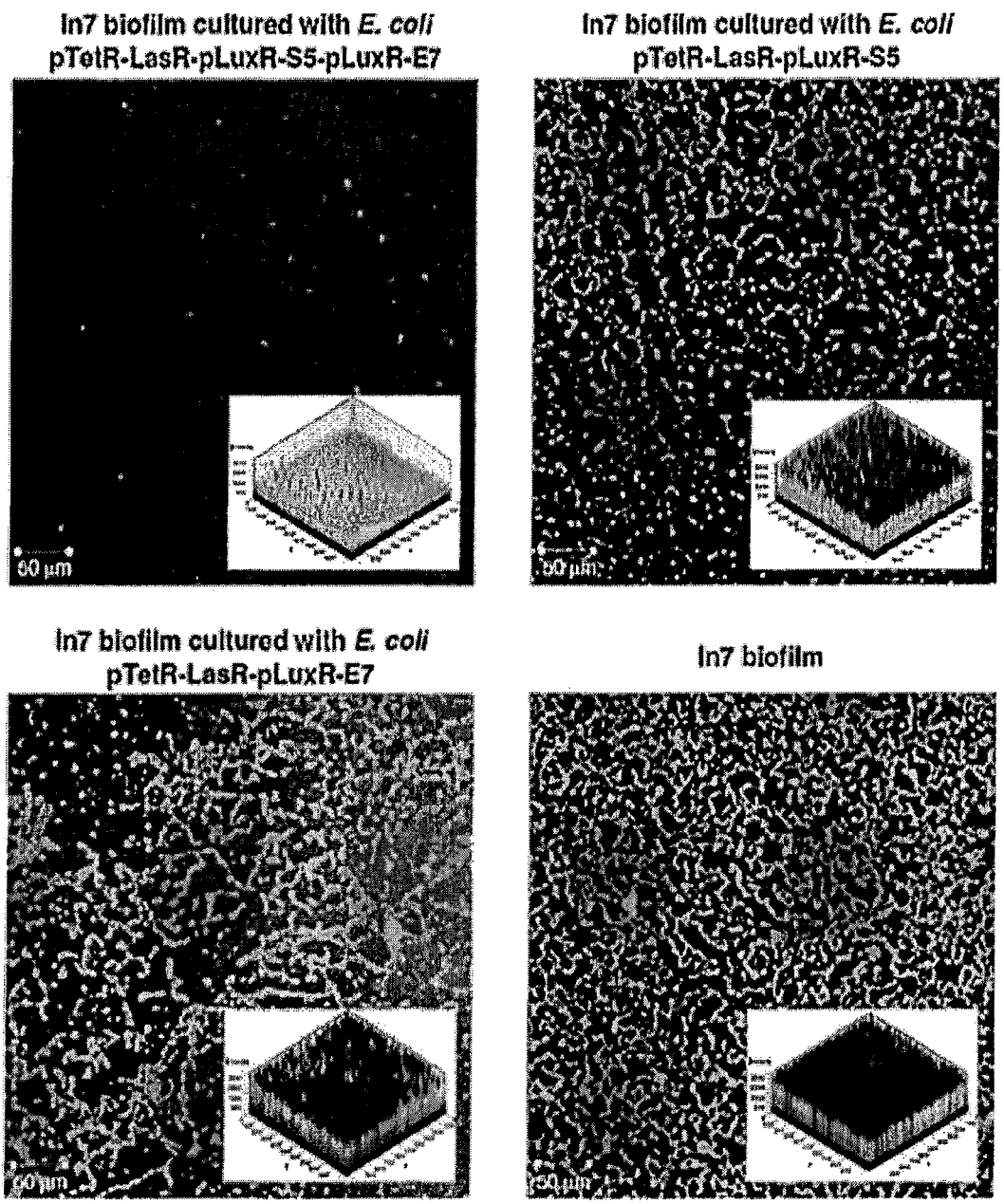
FIG. 6B shows biofilm inhibition observed under CLSM (confocal laser scanning microscopy). *Pseudomonas* biofilm with green fluorescence was grown on glass slide in the presence of the engineered *E. coli* and visualized under CLSM microscope after 18 hrs. Images reconstructed from biofilm Z-stacks using Zeiss 2.5D software implied that the initialization and progression of biofilm cells into multilayers were strongly inhibited for *Pseudomonas* grown with *E. coli* carrying the final system as opposed to lush and elaborated biofilm formation observed in *Pseudomonas* grown alone or with incomplete *E. coli* system missing either pyocin S5 or E7 lysis genes. Scale bar: 50 mm. Z-stack: 40 mm.

To visualize the extent of biofilm inhibition, biofilm cells with green fluorescence were grown in the presence of engineered *E. coli* on glass slide substrate and examined with confocal laser scanning microscopy (CLSM). FIG. 6B shows that the morphology of *Pseudomonas* biofilm treated with the engineered *E. coli* appeared sparse while elaborated honeycombed structures were apparent in the control examples. This observation implies that the engineered *E. coli* in accordance to various embodiments has the capability to inhibit biofilm formation during the initial attachment phase and prevent subsequent progression into mature microcolonies. Collectively, the examples suggest that the engineered *E. coli* carrying the final system, which contains the sensing, killing, and lysing devices, can effectively inhibit the growth of *P. aeruginosa* in both planktonic and sessile states, e.g. biofilm states when those two microbes were grown together.

*E. coli*, a natural inhabitant of the gastrointestinal tract, was chosen as the chassis in this example. It should be understood that the synthetic biology framework and genetic devices developed could potentially be transferred into other microbial chassis such as probiotics and residential microbes of the upper respiratory tract. Further, the possibility of engineering potentially beneficial microbiota into therapeutic bioagents to arrest *Pseudomonas* infection should be appreciated.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. An isolated nucleic acid molecule comprising:
    a first nucleotide sequence encoding a protein that is able to form a complex with an acyl homoserine lactone (AHL) produced by a pathogenic microorganism; and
    a second nucleotide sequence encoding an antimicrobial peptide, wherein the antimicrobial peptide is effective against the pathogenic microorganism, wherein the second nucleotide sequence is under control of a promoter that is induced by the complex of the protein encoded by the first nucleotide sequence and the acyl homoserine lactone (AHL) produced by said pathogenic microorganism, and wherein the protein encoded by the second nucleotide sequence is a bacterocin.

2. The isolated nucleotide acid molecule of claim 1, wherein the nucleic acid molecule further comprises a third nucleotide sequence encoding a protein that is capable of lysing a cell hosting the isolated nucleic acid molecule, wherein said third nucleotide sequence is under control of a promoter that is induced by the complex of the protein encoded by the first nucleotide sequence and the acyl homoserine lactone (AHL) produced by said pathogenic microorganism.

3. The isolated nucleic acid molecule of claim 1, wherein the first nucleotide sequence is under control of a constitutively active promoter.

4. The isolated nucleic acid molecule of claim 1, wherein the protein encoded by the first nucleotide sequence is a transcription factor.

5. The isolated nucleic acid molecule of claim 1, wherein the protein encoded by the first nucleotide sequence is the transcription factor LasR that binds to the AHL N-3-oxododecanoyl homoserine lactone ($3OC_{12}HSL$).

6. The isolated nucleic acid molecule of claim 5, wherein the inducible promoter of the second nucleotide sequence is a luxR promoter that is bound and induced by a complex of LasR and $3OC_{12}HSL$.

7. The isolated nucleic acid molecule of claim 1, wherein the bacteriocin is a pyocin.

8. The isolated nucleic acid molecule of claim 7, wherein the pyocin is pyocin S5.

9. The isolated nucleic acid molecule of claim 1, wherein the protein encoded by the first nucleotide sequence, the protein encoded by the second nucleotide sequence or both are specific for a pathogenic microorganism.

10. The isolated nucleic acid molecule of claim 9, wherein the pathogenic microorganism is selected from the group consisting of Pseudomonas aeruginosa, Clostridium difficile, Escherichia coli, Helicobacter pylori, Salmonella, Vibrio cholera and Yersinia.

11. The isolated nucleic acid molecule of claim 2, wherein the protein encoded by the third nucleotide sequence is a lysis protein that lyses the cell membrane of an E. coli host cell.

12. The isolated nucleic acid molecule of claim 11, wherein the protein encoded by the third nucleotide sequence is the E7 lysis protein.

13. The isolated nucleic acid molecule of claim 2, wherein the inducible promoter of the second nucleotide sequence is a luxR promoter that is bound and induced by a complex of LasR and $3OC_{12}HSL$.

14. The isolated nucleic acid molecule of claim 1, wherein the first nucleotide sequence has the nucleotide sequence set forth in SEQ ID NO:1.

15. The isolated nucleic acid molecule of claim 1, wherein the second nucleotide sequence together with the inducible promoter has the nucleotide sequence set forth in SEQ ID NO:2.

16. The isolated nucleic acid molecule of claim 2, wherein the third nucleotide sequence together with the inducible promoter has the nucleotide sequence set forth in SEQ ID NO:3.

17. The isolated nucleic acid molecule of claim 2, wherein the isolated nucleic acid molecule comprises the nucleotide sequence set forth in SEQ ID NO:4.

18. The isolated nucleic acid molecule of claim 1 comprised in a vector.

19. A recombinant microorganism comprising the isolated nucleic acid molecule of claim 1.

20. A recombinant microorganism comprising the isolated nucleic acid molecule of claim 18.

21. The recombinant microorganism of claim 20, wherein the microorganism is E. coli.

22. A method of sensing and inhibiting the growth of or killing pathogenic microorganisms, the method comprising contacting the recombinant microorganism of claim 19 with the pathogenic microorganism.

23. The method of claim 22, wherein the method is a method of sensing and killing pathogenic microorganisms in a subject, the method comprising administering the recombinant microorganism of claim 19 to said subject.

24. The method of claim 22, wherein the pathogenic microorganism is a human pathogen.

25. The method of claim 22, wherein the pathogenic microorganism is selected from the group consisting of Pseudomonas aeruginosa, Clostridium difficile, Escherichia coli, Helicobacter pylori, Salmonella, Vibrio cholera and Yersinia.

* * * * *